US007148400B1

(12) United States Patent
Meulewaeter et al.

(10) Patent No.: US 7,148,400 B1
(45) Date of Patent: Dec. 12, 2006

(54) METHODS AND MEANS FOR DELIVERING INHIBITORY RNA TO PLANTS AND APPLICATIONS THEREOF

(75) Inventors: Frank Meulewaeter, Eksaarde (BE); Marc Cornelissen, Heusden (BE); John Jacobs, Roosendaal (NL); Gerben Van Eldik, Ghent (BE); Michael Metzlaff, Tervuren (BE)

(73) Assignee: Bayer BioScience N.V., Ghent (BE)

( * ) Notice: Subject to any disclaimer, the term of this patent is extended or adjusted under 35 U.S.C. 154(b) by 0 days.

(21) Appl. No.: 09/551,494

(22) Filed: Apr. 18, 2000

Related U.S. Application Data

(60) Provisional application No. 60/219,314, filed on Apr. 20, 1999, now abandoned.

(51) Int. Cl.
*C12N 15/82* (2006.01)
*C12N 15/83* (2006.01)
*C12N 15/09* (2006.01)

(52) U.S. Cl. .................................... 800/286; 435/320.1

(58) Field of Classification Search ................ 800/295, 800/278–280, 285, 286, 283; 435/419, 468, 435/6, 91.31, 320.1; 536/23.1, 23.6, 24.5
See application file for complete search history.

(56) References Cited

U.S. PATENT DOCUMENTS

| | | | |
|---|---|---|---|
| 5,034,323 A | 7/1991 | Jorgensen et al. | |
| 5,190,931 A | 3/1993 | Inouye | |
| 5,231,020 A | 7/1993 | Jorgensen et al. | |
| 5,283,184 A | 2/1994 | Jorgensen et al. | |
| 5,304,731 A * | 4/1994 | Masuta et al. | |
| 5,500,360 A | 3/1996 | Ahlquist et al. | |
| 5,627,060 A * | 5/1997 | Ahlquist et al. | |
| 6,303,848 B1 * | 10/2001 | Kumagai et al. | 800/300 |

FOREIGN PATENT DOCUMENTS

| | | |
|---|---|---|
| EP | 0 223 388 | 5/1887 |
| EP | 0 194 809 | 9/1986 |
| EP | 0 240 208 | 10/1987 |
| EP | 0 467 349 | 1/1992 |
| EP | 0 647 715 | 4/1995 |
| WO | WO 87-06261 | * 10/1987 |
| WO | WO 90-12107 | * 10/1990 |
| WO | WO93/03161 | 11/1993 |
| WO | WO93/23551 | 11/1993 |
| WO | WO95/34668 | 12/1995 |
| WO | WO96/22364 | 7/1996 |
| WO | WO97/49814 | 12/1997 |
| WO | WO98/53083 | 11/1998 |
| WO | WO 98-53083 | * 11/1998 |
| WO | WO99/07865 | 12/1999 |

OTHER PUBLICATIONS

Routh et al. Characterization of Deletion and Frameshift Mutants of Satellite Tobacco Mosaic Virus. 1995. Virology, vol. 212, pp. 121-127.*

(Continued)

*Primary Examiner*—Ashwin Mehta
(74) *Attorney, Agent, or Firm*—Buchanan Ingersoll & Rooney PC

(57) ABSTRACT

The invention provides methods and means for the identification of genes involved in the determination of a plant trait or for the identification encoded by a nucleic acid comprising a determined nucleotide sequence. The invention also provides kits comprising viral RNA vectors derived from satellite viruses and corresponding helper viruses for the introduction of inhibitory RNA into plant cells and plants.

32 Claims, 1 Drawing Sheet

OTHER PUBLICATIONS

Gossele et al., Plant J., 2002, vol. 32, pp. 859-866.*
Bringloe et al., "The Nucleotide Sequence of Satellite Tobacco Necrosis Virus Strain C and Helper-Assisted Replication of Wild-Type and Mutant Clones of the Virus", *Journal of General Virology* vol. 79, pp. 1539-1546 (1998).
Chapman, Ph.D. Dissertation "A Molecular Analysis of Potato Virus X", University of Cambridge, UK (1991).
Coutts et al., "The Complete Nucleotide Sequence of Tobacco Necrosis Virus Strain D" *J. Gen. Virology* vol. 72, pp. 1521-1529 (1991).
Danthinne et al., "Structural Similarities Between the RNAs of Two Satellites of Tobacco Necrosis Virus" *Virology,* vol. 185, pp. 605-614 (1991).
Depicker et al., "Post-Transcriptional Gene Silencing in Plants" *Curr. Opin. Cell. Biol.* vol. 9, pp. 373-382 (1997).
English et al., "Suppression of Virus Accumulation in Transgenic Plants Exhibiting Silencing of Nuclear Genes", *Plant Cell,* vol. 8, pp. 179-188 (1996).
Hamilton et al., "A Transgene With Repeated DNA Causes High Frequency Post-Transcriptional Suppression of ACC-Oxidase Gene Expression in Tomato" *Plant Journal* vol. 15, No. 6, pp. 737-746 (1998).
Kempin et al., "Targeted Disruption in *Arbidopsis", Nature* vol. 389, pp. 802-803 (1997).
Kumagai et al., "Cytoplasmic Inhibition of Carotenoid Biosynthesis With Virus-Derived RNA" *Proc. Nat. Acad. Sci. USA,* vol. 92, pp. 1679-1683 (1995).
Meulewaeter et al., "Genome Structure of Tobacco Necrosis Virus Strain A", *Virology* vol. 177, pp. 699-709 (1990).
Prashar et al., "Analysis of Differential Gene Expression by Display of 3' End Restriction Fragments of cDNAs", *Proc. Natl. Acad. Sci, USA,* vol. 93, pp. 659-663 (1996).
Ruiz et al., "Initiation and Maintenance of Virus-Induced Gene Silencing", *Plant Cell,* vol. 10, pp. 937-946 (1998).
Stam et al., "The Silence of Genes in Transgenic Plants", *Annals of Botany,* vol. 79, pp. 3-12 (1997).
Takayuki et al., "Construction of an Equalized cDNA Library from *Arabidopsis thaliana", Plant Journal* vol. 8, No. 5, pp. 771-776 (1995).
Waterhouse et al., "Virus Resistance and Gene Silencing in Plants Can be Induced by Simultaneous Expression of Sense and Antisense RNA", *Proc. Natl. Acad. Sci. USA,* vol. 95, pp. 13959-13964 (1998).
Wellink et al., "Cowpea Mosaic Virus Derived Expression Vectors", *Proc. Natl. Acad. Sci USA* Abstract presented at the Joint Meeting of Arbeitskreis Virologie and Nederlandse Kring voor Plantenvirologie in Wageningen, The Netherlands, Nov. 12 and 13, 1998.
Ysebaert et al., "Total Nucleotide Sequence of a Nearly Full-size DNA Copy of Satellite Tobacco Necrosis Virus RNA" *J. Mol. Biol.* vol. 143, pp. 273-287 (1980).
Angell and Baulcombe, "Consistent Gene Silencing in Transgenic Plants Expressing a Replicating Potato Virus X RNA", *EMBO Journal,* vol. 16, No. 12, pp. 3675-3684 (1997).
Baulcombe, "Mechanisms of Pathogen-Derived Resistance to Viruses in Transgenic Plants", *Plant Cell,* vol. 8, pp. 1833-1844 (1996).
Baulcombe et al., "Virus-Induced Gene Silencing", *JIC&SL Annual Report* (1996/1997).
E. Rodriguez-Cerezo et al., "Genetic Heterogeneity of the RNA Genome Population of the Plant Virus U5-TMV", *Virology*, vol. 170, p. 418-423 (1989) Academic Press, Inc. San Diego, California USA.
C. Kearney et al., "Low Level of Genetic Drift in Foreign Sequences Repilcating in an RNA Virus in Plants", *Virology*, vol. 192, p. 11-17 (1993) Academic Press, Inc. San Diego, California USA.
G. Kurath et al., "RNase Protection Analyses Show High Genetic Diversity among Field Isolates of Satellite Tobacco Mosaic Virus", *Virology*, vol. 194, p. 414-418 (1993) Academic Press, Inc. San Diego, California USA.
G. Kurath et al., "Tobamovirus Helper Specificity of Satellite Tobacco Mosaic Virus Involves a Domain Near the 5' End of the Satellite Genome", *Journal of General Virology*, vol. 74, p. 1233-1243 (1993) SGM, Reading, United Kingdom.
G. Kurath et al., "Mutation Analyses of Molecularty Cloned Satellite Tobacco Mosaic Virus During Serial Passage in Plants: Evidence for Hotspots of Genetic Change", *RNA*, vol. 1 p. 491-500 (1995), RNA Society, Palo Alto, California.
F. Garcia-Arenal et al., "Variability and Genetic Structure of Plant Virus Populations", *Annu. Rev. Phytopathol. 2001*, vol. 39, p. 157-86, *Annual Reviews*, Palo Alto, California.
R. Joshi et al., "Strategies for Expression of Foreign Genes in Plants", *FEBS*, vol. 281, No. 1,2, p. 1-8, Elsevier Science Publishers B.V., Oxford, United Kingdon (1991).
J. Donson et al., "Systemic Expression of a Bacterial Gene by a Tobacco Mosaic Virus-Based Vector", *Proc. Natl. Acad. Sci USA*, vol. 88, p. 7204-7208 (Aug 1991) Genetics, Chicago, Illinois.
D. Baulcombe et al., "Fast Forward Genetics Based on Virus-Induced Gene Silencing", *current Opinion in Plant Biology*, vol. 2, p. 108-113 (1999), Elsevier Science Ltd. ISSN 1369-5266, Oxford, United Kingdom.
J. Lindbo et al. "Virus-Mediated Reprogramming of Gene Expression in Plants", *Current Opinion in Plant Biology 2001*, vol. 4, p. 181-185, Elsevier Science Ltd., Oxford, United Kingdom.
M. Ruiz et al., "Initiation and Maintenance of Virus-Induced Gene Silencing", *The Plant Cell*, vol. 10, p. 937-946 (1998). The American Society of Plant Physlolgists, Rockville, Maryland.
G. Routh et al., "Characterization of Deletion and Frameshift Mutants of Satellite Tobacco Mosaic Virus", *Virology*, vol. 212, p. 121-127 (1995), Academic Press, Inc. San Diego, California USA.
T. Mirkov et al., "Factors Affecting Efficient Infection of Tobacco with *in Vitro* RNA Transcripts from Cloned cDNAs of Satlelite Tobacco Mosaic Virus", *Virology*, vol. 179, p. 395-402 (1990), Academic Press, Inc. San Diego, California USA.
M. Kumagal et al., "Cytoplasmic Inhibition of Carotenoid Biosynthesis with Virus-Derived RNA", *Proc. Natl. Acad. Sci., USA*, vol. 92, P. 1679-1683, (Feb. 1995), Genetics, Chicago, Illinois.
W. Qiu et al., "Defective Interfacing RNAs of a Satellite Virus", *Journal of Virology, Jun. 2001*, p. 5429-5432, American Scoeity for Microbiology, Washington, D.C.
A. Simon, "Satellite RNAs of Plant Viruses", *Plant Molecular Biology Reporter*, vol. 6(4), p. 240-252 (1988).

* cited by examiner

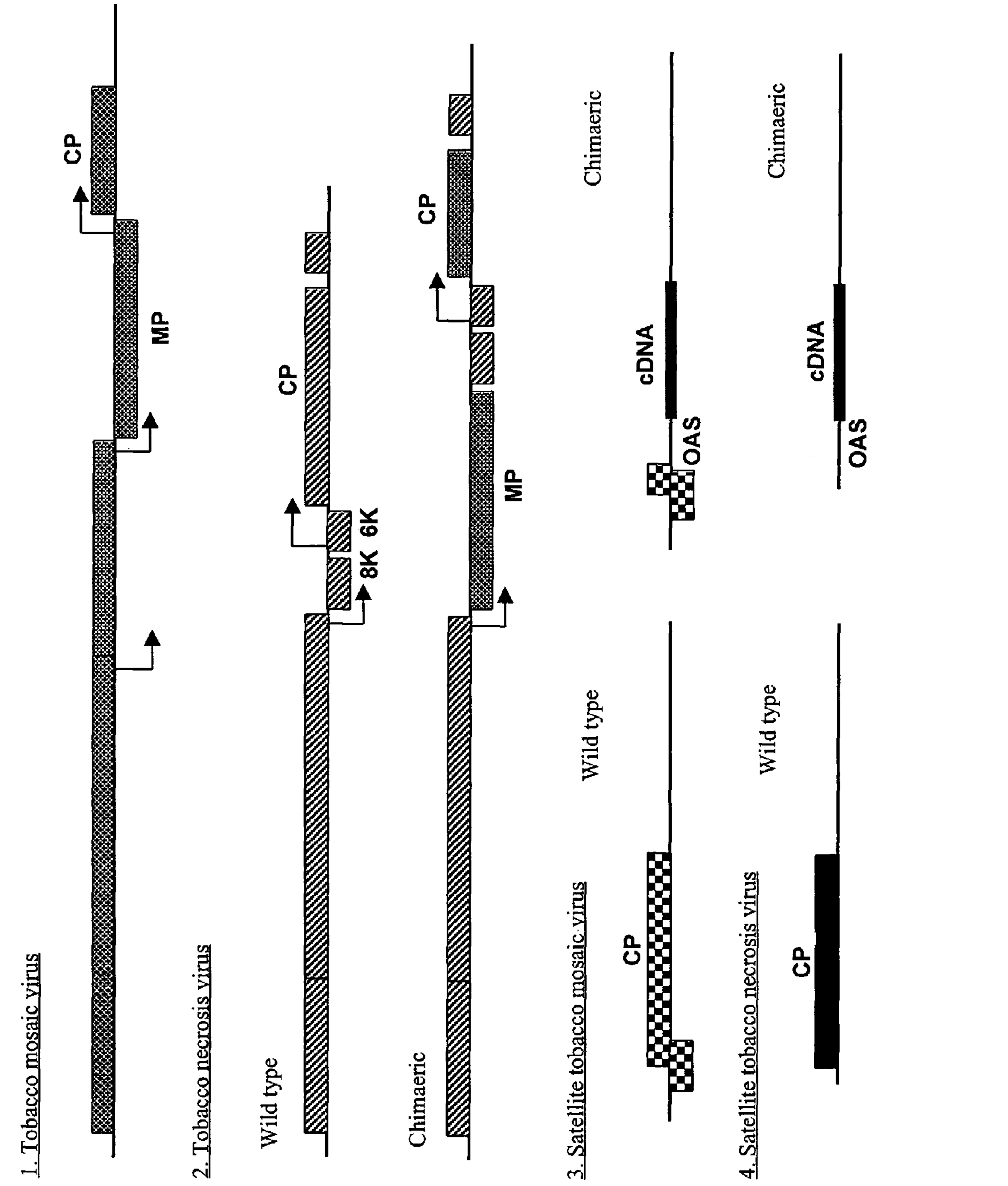
1. Tobacco mosaic virus
CP
MP
2. Tobacco necrosis virus
Wild type
CP
8K
6K
Chimaeric
CP
MP
3. Satellite tobacco mosaic virus
CP
Wild type
Chimaeric
cDNA
OAS
4. Satellite tobacco necrosis virus
CP
Wild type
Chimaeric
cDNA
OAS

METHODS AND MEANS FOR DELIVERING INHIBITORY RNA TO PLANTS AND APPLICATIONS THEREOF

CROSS-REFERENCE TO RELATED APPLICATIONS

This application is a continuation-in-part of U.S. provisional application Ser. No. 60/219,314, filed Apr. 20, 1999 now abandoned, the contents of which are incorporated herein by reference.

FIELD OF THE INVENTION

This invention relates to the field of functional genomics in plants, more particularly it relates to methods for the further identification and isolation of a nucleic acid with a nucleotide sequence of interest in a collection of preselected nucleic acid sequences correlated with a particular trait, preferably an agronomical important trait, using a kit of viral RNA vectors which allow systemic spread of all components of the kit in a plant, wherein one of the viral RNA vectors comprises a library of gene-silencing constructs for the preselected nucleic acid sequences. The invention also relates to a method for modulating, preferably reducing, particularly eliminating the expression of a selected nucleic acid sequence, using the viral vector kit, whereby one of the vectors comprises a gene-silencing construct for the selected nucleic acid sequence. The latter method may be used for validating the function of a nucleic acid sequence whose expression is correlated with the presence or absence of a specific trait in plants, but with otherwise unknown function. Preferably, one of the viral RNA vector components of the kit is a vector derived from a satellite virus.

BACKGROUND ART

The recent, rapid expansion of available nucleic acid sequence information has necessitated the development of methods for identifying the function of nucleic acid sequences, particularly transcribed nucleic acid sequences such as expressed sequence tags, with unknown function, in an efficient and labor-cost effective way.

To identify the role of sequenced nucleic acids from plants of unknown function it is necessary to produce or identify plants in which those nucleic acids are either structurally or functionally inactivated. Plants wherein predetermined nucleic acid sequences are structurally inactivated can be generated using recombination technologies such as homologous recombination as described by Kempin et al. (1997) or using specific technologies such as the use of mixed duplex oligonucleotides (chimeraplasts) to generate specific mutations (as described in WO 96/22364 and WO 99/07865). Alternatively, plants with a mutation in a predetermined nucleotide sequence can be identified by screening a saturated mutant library, such as but not limited to a T-DNA insertion library or a transposon insertion library (see e.g. Pereira and Aerts, 1998). These methodologies all require the generation of a large number of permanently altered plants, and thus are less amenable for application in high throughput methods. Moreover, the recovery of plants with recessive mutations in essential genes requires time-consuming breeding to maintain the plants in heterozygous state. Maintenance of dominant lethal mutations in essential genes is virtually impossible.

Plants with functionally inactivated predetermined nucleotide sequences can be generated in a straightforward way using methodologies wherein inhibitory RNA is generated, such as antisense or sense RNA.

The use of inhibitory RNA to reduce or abolish gene expression, also known as gene silencing, is well established in the art and is the subject of several reviews (e.g Baulcombe 1996, Stam et al. 1997, Depicker and Van Montagu, 1997). Several patent applications relate to the practical exploitation of gene silencing.

U.S. Pat. No. 5,190,131 and EP 0 467 349 A1 describe methods and means to regulate or inhibit gene expression in a cell by incorporating into or associating with the genetic material of the cell a non-native nucleic acid sequence which is transcribed to produce an mRNA which is complementary to and capable of binding to the mRNA produced by the genetic material of that cell.

EP 0 240 208 describes a method to regulate expression of genes encoded for in plant cell genomes, achieved by integration of a gene under the transcriptional control of a promoter which is functional in the host and in which the transcribed strand of DNA is complementary to the strand of DNA that is transcribed from the endogenous gene(s) one wishes to regulate.

EP 0 223 399 A1 describes methods to effect useful somatic changes in plants by causing the transcription in the plant cells of negative RNA strands which are substantially complementary to a target RNA strand. The target RNA strand can be a mRNA transcript created in gene expression, a viral RNA, or other RNA present in the plant cells. The negative RNA strand is complementary to at least a portion of the target RNA strand to inhibit its activity in vivo.

EP 0 647 715 A1 and U.S. Pat. Nos. 5,034,323, 5,231,020 and 5,283,184 describe methods and means for producing plants exhibiting desired phenotypic traits, by selecting transgenotes that comprise a DNA segment operably linked to a promoter, wherein transcription products of the segment are substantially homologous to corresponding transcripts of endogenous genes, particularly endogenous flavonoid biosynthetic pathway genes.

WO 93/23551 describes methods and means for the inhibition of two or more target genes, which comprise introducing into the plant a single control gene which has distinct DNA regions homologous to each of the target genes and a promoter operative in plants adapted to transcribe form such distinct regions RNA that inhibits expression of each of the target genes.

A major disadvantage of these technologies, which hampers the exploitation thereof in high throughput gene function discovery methods, is the intrinsic unpredictability and low occurrence of the gene silencing phenomenon.

Recently, Waterhouse et al. (1998) have described methods and means to make gene silencing in plants more efficient and predictable, by simultaneous expression of both sense and antisense constructs in cells of one plant. The sense and antisense nucleic acids may be in the same transcriptional unit, so that a single RNA transcript that has self-complementarity is generated upon transcription.

Hamilton et al. (1998) describe improved silencing e.g. of tomato ACC-oxidase gene expression using a sense RNA containing two additional upstream inverted copies of its 5' untranslated region.

WO 98/53083 describes constructs and methods for enhancing the inhibition of a target gene within an organism, involving the insertion into the gene silencing vector of an inverted repeat of all or part of a polynucleotide region within the vector.

It should be clear however, that the use of inhibitory RNA as a tool in reversed genetics analysis of gene function via high throughput methods, whereby the inhibitory RNA is generated from gene-silencing constructs which are stably integrated in the genome of transgenic plants, suffers from the same drawbacks as the methods wherein the nucleotide sequences are structurally inactivated.

EP 0 194 809 and U.S. Pat. No. 5,500,360 suggest the use of viral RNA vectors to produce regulatory RNA such as anti-sense RNA.

Initial exploration of the use of viral vectors to deliver inhibitory RNA into cells of plants has been described by Chapman (1991). In this publication, gene silencing constructs comprising nucleotide sequences complementary to the translated region of the GUS gene on a PVX derived viral vector were described. The experiments however, remained inconclusive as to whether gene silencing could be provoked using viral vectors for the production of inhibitory RNA.

WO 93/03161 is directed toward recombinant plant viral nucleic acids and to hosts infected thereby. The non-native nucleic acid sequence which is transcribed may be transcribed as an RNA which is capable of regulating the expression of a phenotypic trait by an anti-sense mechanism.

English et al., 1996 describe the suppression of the accumulation of a viral vector comprising a foreign nucleotide sequence in transgenic plants exhibiting silencing of nuclear genes comprising the same foreign nucleotide sequences, thus linking gene silencing and viral vectors, albeit in a reverse way as envisioned here.

Kumagai et al. 1995 (PNAS 92, 1679–1683) described the inhibition of phytoene desaturase gene by viral delivery of antisense RNA.

WO 95/34668 suggests the use of genetic constructs based on RNA viruses which replicate in the cytoplasm of cells to provide inhibitory RNA, either antisense or co-suppressor (sense) RNA.

Baulcombe et al. (1998) and Ruiz et al. (1998) describe virus-induced gene silencing of the endogenous phytoene desaturase gene (PDS) or of a green fluorescent protein transgene (GFP) in plants, using potato virus X derived vectors carrying inserts homologous to PDS and GFP, respectively. The authors further suggested that virus-induced gene silencing may develop into a novel assay of gene function, by introducing a fragment of the genome of a viral vector and inferring the function of the gene from the symptoms of the infected plants exhibiting gene silencing.

The described methods for identification of the function of a gene with known nucleotide sequence however, have drawbacks and limitations. In the first place, the applicability of the mentioned viral RNA vector based gene silencing methods on larger scale is in practice limited to the identification of genes with essential functions or genes with macroscopically visible phenotypes. Secondly, all methods employ viral vectors which are capable of autonomous replication in plant cells and cell-to-cell movement, whereby care has to be taken not to inactivate the essential functions required for these functions. This may particularly be a disadvantage when tailoring these methods to the needs of particular plants, such as crop plants, by developing new viral vectors more apt for replication and systemic spread in the plants.

The prior art is thus deficient in the lack of efficient methods for large scale identification of the function of nucleic acids with known nucleotide sequence, or for the isolation of the genes of interest from a pool of genes with known nucleotide sequence, but unknown function.

BRIEF DESCRIPTION OF THE FIGURES

FIG. 1 is a schematic representation of the viral RNA vectors used in the Examples. MP: movement protein; CP: coat protein; OAS: origin of assembly. The open reading frames are indicated by boxes. Each original viral genome is characterized by a specific pattern.

▨: tobacco mosaic virus; ▧ tobacco necrosis virus; ▩ satellite tobacco mosaic virus; ■ satellite tobacco necrosis virus.

SUMMARY OF THE INVENTION

The invention provides a method for isolating genes involved in the determination of a trait or a phenotype of a plant species, comprising identifying a set of nucleic acids sequences of genes, whose expression is correlated with a trait of interest; creating a library of gene silencing constructs targeted or adapted to the nucleotide sequence of the identified nucleic acids in a viral RNA vector which is capable of replication inside plant cells and optionally, movement between plant cells of a plant; infecting a collection of individual plants of the same plant species with the library of gene silencing constructs whereby each plant is infected with at least one member of the library; identifying a plant wherein the trait or phenotype is altered using an assay adapted to that trait or phenotype; and isolating the gene involved in the determination of the trait or phenotype in the plant species, from the library, based on the nucleotide sequence to which the gene silencing construct in the identified plant was targeted. Preferably the viral RNA vector is capable of autonomous replication inside plant cells and optionally autonomous movement between plant cells and particularly the viral RNA vector is derived from cowpea mosaic virus.

Alternatively, the viral RNA vector, is derived from a satellite RNA virus, preferably satellite tobacco mosaic virus or satellite tobacco necrosis virus, particularly it further comprises an origin of assembly of tobacco mosaic virus, and is capable of replication inside plant cells and optionally movement between plant cells when the required factors are supplemented in trans, preferably by infection with a helper virus, preferably tobacco mosaic virus or a helper virus which is derived from tobacco necrosis virus and comprises a gene encoding a coat protein gene of tobacco mosaic virus, and optionally, a movement protein of tobacco mosaic virus.

Gene-silencing constructs comprised within the viral RNA vector may comprise antisense RNA or sense RNA, preferably they may comprise an inverted repeat. Particularly the gene-silencing constructs comprise complementary stretch of at least 50, preferably at least 100 nucleotides of sense and antisense RNA. Especially preferred are gene-silencing constructs comprising at least two copies of part of the nucleotide sequences of the collection of nucleic acids, the copies being in inverted repeat.

It is another object of the invention to provide a method for the isolation or selection of a nucleic acid with a specific function from a collection of nucleic acids, wherein the collection of nucleic acids is characterized by the fact that variation in the expression pattern of the nucleic acids is correlated with variation in a trait or phenotype of a plant harboring the nucleic acids comprising the steps of creating a library of gene silencing constructs targeted or adapted to the nucleotide sequence of the identified nucleic acids in a viral RNA vector which is capable of replication inside and optionally movement between plant cells; infecting a collection of plants with the library of gene silencing constructs, whereby each plant is infected with one member of the library; identifying plants with altered trait or phenotype using an assay adapted to the trait or phenotype under investigation; and optionally isolating the nucleic acid with the specific function from the identified plant with altered trait or phenotype.

It is yet another object of the invention to provide a method for determining the function encoded by a nucleic acid comprising a known nucleotide sequence in a plant, comprising the steps of providing a viral RNA vector derived from a satellite RNA virus, comprising a gene-silencing construct targeted to a gene comprising the known nucleotide sequence; infecting or inoculating the plant with the chimeric viral RNA vector and a corresponding helper virus or helper virus RNA; and identifying an altered trait or phenotype of the co-infected plant.

The invention further provides a method for isolating essential genes from a plant, comprising creating a library of random gene-silencing constructs, preferably by cloning random DNA fragments of the plant or by cloning random cDNA fragments, particularly duplicated cDNA fragments in inverted repeat in a cDNA copy of the viral RNA vector derived from a satellite RNA virus, preferably STMV or STNV, particularly a viral RNA vector comprising an origin of assembly of TMV; infecting a plant with individual members of the library and with a corresponding helper virus, preferably tobacco mosaic virus or a helper virus derived from tobacco necrosis virus and comprising the coat protein of tobacco mosaic virus and optionally the movement protein; identifying plants developing gene-silencing-construct-associated necrosis and optionally isolating the viral RNA vector from the necrotized tissue.

It is yet another object of the invention to provide a method for introduction of inhibitory RNA, preferably sense or antisense RNA, particularly inhibitory RNA comprising an inverted repeat, especially inhibitory RNA comprising a complementary stretch of at least 50, preferably at least 100 nucleotides of sense and antisense RNA, into plant cells, preferably into the cytoplasm of plant cells, comprising introducing into a plant cell, a viral RNA vector comprising the inhibitory RNA or comprising a chimeric nucleic acid which when transcribed yields the inhibitory RNA, wherein the viral RNA vector is derived from a satellite RNA virus, preferably STMV or STNV, particularly a STMV—derived or STNV derived RNA vector comprising an origin of assembly from tobacco mosaic virus; and introducing into the same plant cell, a corresponding helper virus, preferably tobacco mosaic virus or a chimeric helper virus derived from tobacco necrosis virus and comprising a coat protein gene of tobacco mosaic virus and optionally, a movement protein encoding gene of tobacco mosaic virus.

The invention further provides a kit for introduction of inhibitory RNA, preferably sense or antisense RNA, particularly inhibitory RNA comprising an inverted repeat, especially inhibitory RNA comprising a complementary stretch of at least 50, preferably at least 100 nucleotides of sense and antisense RNA in the cytoplasm of a plant cell comprising 1) a viral RNA vector derived from a satellite RNA virus, comprising the inhibitory RNA or which comprise a chimeric nucleic acid which when transcribed yields the inhibitory RNA; and 2) a corresponding helper virus.

A particularly preferred kit comprises 1) a viral RNA vector derived from a satellite tobacco mosaic virus, comprising an origin of assembly of tobacco mosaic virus, further comprising or encoding the inhibitory RNA; and 2) a corresponding helper virus derived from a tobacco mosaic virus.

Another particularly preferred kit comprises 1) a viral RNA vector derived from satellite tobacco necrosis virus, especially STNV-2 or STNV-C and comprising an origin of assembly of tobacco mosaic virus further comprising or encoding the inhibitory RNA; and 2) a corresponding helper virus derived from tobacco necrosis virus, particularly TNV-A or TNV-D, which comprises a coat protein gene of tobacco mosaic virus and optionally a movement protein gene of tobacco mosaic virus.

DETAILED DESCRIPTION OF PREFERRED EMBODIMENTS

The following definitions apply throughout this application, unless otherwise specified.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

As used herein, "a trait of a plant" indicates a phenotype which is the combined result of the coordinated expression of a number of genes. Typical traits include yield, heterosis, drought-resistance, stress-resistance, high or low temperature-resistance, vigor, seed yield, plant habitat, architecture etc. Typically, a trait of a plant is named after its intended appearance.

A used herein a "phenotype" of a plant refers to any quantitative or qualitative characteristic of that plant, be it morphological (including macroscopic and microscopic characteristics), biochemical (including the presence, absence or concentration of particular metabolites or molecules) functional or other.

The term "gene" means any DNA or RNA fragment comprising a region (the "transcribed region") which is transcribed into a RNA molecule (e.g., a mRNA) in a cell, operably linked to suitable regulatory regions, e.g., a plant-expressible promoter. A gene may thus comprise several operably linked fragments such as a promoter, a 5' leader sequence, a coding region, and a 3' region comprising a polyadenylation site. A plant gene endogenous to a particular plant species or virus (endogenous plant or virus gene) is a gene which is naturally found in that plant species or virus, or which can be introduced in that plant species by breeding techniques such as conventional breeding techniques. A chimeric gene is any gene which is not normally found in a plant species or, alternatively, any gene in which the promoter is not associated in nature with part or all of the transcribed DNA region or with at least one other regulatory region of the gene.

The term "expression of a gene" refers to the process wherein a DNA or RNA region which is operably linked to appropriate regulatory regions, particularly to a promoter, is transcribed into an RNA which is biologically active i.e., which is either capable of interaction with another nucleic acid or which is capable of being translated into a biologically active polypeptide or protein. A gene is said to encode an RNA when the end product of the expression of the gene is biologically active RNA, such as e.g. an antisense RNA, a ribozyme or a replicative intermediate. A gene is said to encode a protein when the end product of the expression of the gene is a biologically active protein or polypeptide. In addition to the above defined elements, a gene may further comprise elements for cap-independent translation such a an internal ribosome entry sequence or the first and second translation enhancing elements as defined in WO 97/49814.

As used herein the terms "gene-silencing" or "inhibitory" are not to be interpreted as meaning a complete abolishing of the expression of the target gene(s) but also includes any reduction in expression, measured either as a reduction in transcription and/or translation, as a reduction in the accumulation of transcripts or translation products such as proteins, or as a reduction in the phenotypic expression of the target gene.

The term "reduction of phenotypic expression" refers to the comparison of the phenotypic expression of the nucleic acid of interest in the eukaryotic cell in the presence of the inhibitory RNA or gene-silencing constructs of the invention, to the phenotypic expression of the nucleic acid of interest in a similar eukaryotic cell in the absence of the inhibitory RNA or gene-silencing constructs of the invention. The phenotypic expression in the presence of the inhibitory RNA of the invention should thus be lower than the phenotypic expression in absence thereof, preferably be only about 25%, particularly only about 10%, more particularly only about 5% of the phenotypic expression in absence of the inhibitory RNA, especially the phenotypic expression should be completely inhibited for all practical purposes by the presence of the inhibitory RNA or the gene-silencing construct encoding such an RNA.

A reduction of phenotypic expression of a nucleic acid where the phenotype is a qualitative trait means that in the presence of the inhibitory RNA, the phenotypic trait switches to a different discrete state when compared to a situation in which such inhibitory RNA is absent. A reduction of phenotypic expression of a nucleic acid may thus also be measured as a reduction in transcription of (part of) that nucleic acid or reduction in the level of transcript, a reduction in trans lation of (part of) that nucleic acid or reduction in the level of translation products, or a reduction of the effect the presence of the transcribed RNA(s) or translated polypeptide(s) have on the eucaryotic cell or the organism, and will ultimately lead to altered phenotypes. It is clear that the reduction in phenotypic expression of a nucleic acid of interest, may be accompanied by or correlated to an increase in a phenotype or trait.

In one embodiment of the invention, a method is provided to identify and isolate genes involved in the determination of a trait or a phenotype of a plant. To this end, nucleic acid sequences are identified whose expression is correlated with the trait and/or phenotype of interest. Methods and means are available in the art for the almost simultaneous identification and/or isolation of a large number, if not the predominant part, of nucleotide sequences whose expression, particularly whose transcription, is influenced subsequent to a stimulus corresponding to the trait to be investigated, in comparison with expression of these nucleotide sequences in a control plant. Such methods include but are not limited to differential display methods, such as the gel-based RNA differential display methods described by (Prahasar et al. 1996) As a result of these methods, a collection of at least partially characterized nucleotide sequences with altered expression in response to a particular stimulus is identified. Typically, however, the application of such methods does not allow to discriminate between genes whose altered expression is directly caused by the stimulus, and those who are further downstream in the chain of events and are only indirectly influenced by the stimulus and a further selection amongst the obtained collection of nucleotide sequences will be required. Even less do these methods allow to predict whether the inverse relationship also holds, i.e. whether influencing the expression of genes with particular nucleotide sequences, identified in the above mentioned way, also influences the trait of interest. A further validation of the obtained sequences is thus required, and preferably one which immediately verifies the above mentioned inverse relationship. To achieve this goal in a efficient and cost-effective way, a library of gene-silencing constructs may be created in a viral RNA vector which is capable of replication inside plant cells and movement between cells of a plant, so as to assure an efficient systemic spread within a plant which has been infected with a clone of such a library. The created library of gene-silencing constructs comprised within a viral RNA vector is then used to infect a representative number of plants in such a way that at each plant is infected by at least one member (one clone) of the library. The infected plants can than be analyzed to identify those plants which exhibit alterations in the trait under investigation, using an assay which is adapted to the trait under investigation. It is clear that this fine-tuning of assay and trait under investigation may be an important advantage over the existing methods for high throughput analysis, particularly when analyzing traits and/or phenotypes which do not result in macroscopically visible alterations, such as but not limited to modifications in specific metabolic pathways or alterations which are only detectable under specific conditions (e.g. heat, stress, drought-tolerance, pathogen-infection, application of specific herbicides or insecticides etc.).

The subset of nucleic acid sequences may also be identified on the basis of the presence of a particular signature characteristic of a class of proteins, such as but not limited to a kinase-specific domain, a binding motif etc.

The gene-silencing construct may then be isolated from the library or from the plant exhibiting the altered trait or phenotype, and be used to isolate the corresponding gene based on the nucleotide sequence towards which the gene silencing construct was targeted.

In a preferred embodiment, the viral RNA vector is capable of autonomous replication inside plant cells and autonomous movement between plant cells. Such viral RNA vectors are known in the art and may be based on Potato Virus X as described e.g. in WO 93/03161, WO95/34668, Ruiz et al. (1998)

In a particularly preferred embodiment, the used viral RNA vector is derived from cowpea mosaic virus. Wellink et al. (1998) have described the use of a viral vector derived from this RNA virus for the expression of GFP in plants and demonstrated that the virus and RNA vectors derived thereof have an excellent capacity for spreading throughout an infected plant, particularly *Nicotiana benthamiana*. CPMV is an icosahedral virus with a bipartite RNA genome, consisting of a longer and a shorter RNA. Wellinck et al. have demonstrated that it is possible to incorporate extra genetic information in the shorter RNA, by inserting the GFP coding region in frame into the viral encoded polyprotein. For the purpose of the herein described methods, it is preferred that the inhibitory RNA encoding nucleic acid be inserted downstream of the polyprotein encoding open reading frame.

The inventors have obtained for the first time indications that gene-silencing may be obtained in plant cells such as protoplasts, using a viral vector derived from a satellite virus comprising a β-1,3-glucanase coding region, in a co-infection experiment with a helper virus of the satellite virus.

In another preferred embodiment, the viral RNA vector is capable of replication and cell-to-cell movement, only when the required functions are provided in trans. Particularly preferred, is the use of a satellite virus derived RNA vector, which can replicate in plant cells and spread throughout the plant, when a corresponding helper virus is present.

As used herein, "a satellite virus" indicates an RNA virus, preferably a single stranded RNA virus, the RNA genome of which is capable of replicating in a plant cell and being encapsidated by coat protein molecules to form a virus particle or virion, only when provided externally with any number of required essential functions therefor. By "externally provided" is meant that such functions are not encoded by the satellite viral genome. Satellite viruses thus depend upon external provision of essential functions, and may lack the capacity to encode functional replicase, movement protein, or other essential functions required to complete their life cycle inside a plant cell. In a natural situation, such essential functions are usually provided by an autonomously replicating virus or so-called helper virus.

Satellite viruses useful for the present invention may include wild type isolates, but also encompassed by this definition are variants which result in reduced or minimal symptoms when infected on a host plant, particularly when co-inoculated with a corresponding helper virus. The definition also includes synthetic satellite viruses such as defective viruses and chimeric satellite viruses.

A "viral RNA vector derived from a satellite virus" should at least include cis elements from a satellite virus which are recognized by an externally provided replicase, and an origin of assembly allowing encapsidation by the provided coat protein. Preferably, the viral RNA vector does not comprise a gene encoding a functional coat protein, particularly it does not comprise the nucleotide sequence which is essentially similar to the nucleotide sequence encoding a coat protein gene. Particularly preferred are viral RNA vectors comprising an origin of assembly recognized by coat protein molecules from a rod-shaped virus, such as tobacco mosaic virus, since rod-shaped viruses do not exhibit the spatial constraints imposed on the size of genome by icosahedral viruses, thus allowing a larger number of additional nucleotides to be incorporated in the viral vector. Conveniently, the viral RNA vector comprises a number of unique or low-occurrence restriction recognition sites.

The use of viral RNA vectors derived from a satellite virus, additionally solves problems associated with the use of viral RNA vectors, such as reducing the size of the vectors, increasing versatility etc.

Particularly suited for the invention are viral RNA vectors derived from satellite tobacco mosaic virus comprising the origin of assembly (OAS) from TMV, preferably comprising the nucleotide sequence of SEQ ID No 2 from the nucleotide at position 5443 to the nucleotide at position 5518 or the nucleotide of SEQ ID No 5 from the nucleotide at position 5430 to the nucleotide at position 5505 (such as the nucleotide sequence of SEQ ID No 12) and wherein the coat protein encoding gene has been deleted. Also particularly suited for the invention are viral RNA vectors derived from satellite necrosis vector strain comprising the OAS from TMV and wherein most of the coat protein gene has been deleted. Non-limiting examples of viral RNA vectors, suitable for the invention are described hereinafter.

"A corresponding helper virus" as used herein, indicates those RNA viruses, preferably singe stranded RNA viruses, which can supply the satellite virus or the derived viral RNA vector with the functions required in trans by that satellite virus or the derived viral RNA vector, to allow it to replicate in the cytoplasm of plant cells, and spread throughout an infected plant. Typically, corresponding helper viruses will provide the satellite virus or the vector derived thereof with a replicase (RNA dependent RNA polymerase) which recognizes the cis sequences present on the satellite virus RNA, and will allow replication of the satellite virus genome or the derived vector. Other proteins which may typically be provided by the helper virus are movement proteins, allowing inter alia, the plasmodesmata-mediated spread of viral particles from cell to cell. For satellite viruses or viral RNA vectors derived thereof which lack a functional coat protein encoding gene, corresponding helper viruses may also provide a functional coat protein. Preferably, the corresponding helper virus will be capable of autonomous systemic spread in an infected plant. However, such a systemic spread seems not to be a prerequisite for efficient gene silencing. Functions required in trans for one particular viral RNA vector may be supplied in trans by different corresponding helper viruses.

It is clear that the corresponding helper viruses may be wild type isolates of RNA viruses, preferably single-stranded RNA viruses such as the tobamoviruses or necroviruses. Particularly preferred are rod-shaped RNA viruses such as tobamoviruses including tobacco mosaic virus and the related tobamoviruses such as ribgrass mosaic virus, turnip vein clearing virus, chines rape mosaic virus, oilseed rape mosaic virus.

When TMV can be used as a helper virus, it can also be replaced by one of the closely related tobamoviruses mentioned above, particularly when using the viral vectors in particular plant species.

Also encompassed by the methods and means of the invention are variants of such wild type isolates, preferably variants or mutants which develop minimal symptoms when inoculated on host plants or when co-infected with a corresponding satellite virus or RNA vector derived thereof. Further preferred helper viruses may be variants or mutants of wild type isolates which have an extended host range such as tobamoviruses which can replicate and spread in corn or brassicae.

However, corresponding helper viruses may also be chimeric or hybrid viruses, wherein part of the viral genome has been replaced by a foreign nucleic acid, particularly wherein part of the viral genome has been replaced by a nucleic acid derived from another viral genome, preferably a part comprising a nucleotide sequence encoding a movement protein, or a part comprising a nucleotide sequence encoding a coat protein. E.g. when using a necrovirus such as TNV, it may be advantageous to insert a movement protein encoding region preferably a movement protein derived from a tobamovirus such as TMV, particularly the nucleotide sequence of SEQ ID No 2 from the nucleotide at position 4903 to the nucleotide at position 5709, so as to ensure spreading of the viral particles beyond the infected leaf. However, spreading of the helper virus or the viral RNA vector is not essential for efficient inactivation of expression of the target genes throughout the plant, as was found by the inventors. Also when using e.g. a necrovirus such as TNV, it may be further advantageous to replace the coat protein coding region of the necrovirus by a coat protein coding region of a rod-shaped virus, such as TMV, particularly the nucleotide sequence of SEQ ID No 2 from the nucleotide at position 5712 to the nucleotide at position 6191. It goes without saying that an appropriate origin of assembly for the substituted coat protein has to be incorporated in the genome of the chimeric helper virus. In the above described example however, the OAS of TMV is conveniently located within the movement protein coding region. Non-limiting examples of corresponding helper viruses will be described hereinafter.

It should be clear that whenever it is stated that plants are co-infected or infected with a viral RNA vector and a corresponding helper virus, it is equal whether the helper virus is inoculated before, after or simultaneous with the viral RNA vector, provided however that there is a reasonable time limit between infection of the viral RNA vector or the corresponding helper virus.

Alternatively, the required functions in trans for the replication and movement of the viral RNA vector may be provided from the expression of chimeric genes, encoding a replicase (RNA dependent RNA polymerase) and/or a movement protein and/or a functional coat protein, integrated in the genome of the test plants.

Preferred kits to deliver inhibitory RNA or gene-silencing constructs to plant cells to be used in the herein disclosed methods comprise a viral RNA vector derived from a satellite RNA virus, particularly from satellite tobacco necrosis vector (STNV) or satellite tobacco mosaic virus (STMV) and a corresponding helper virus, particularly a rod-shaped corresponding helper virus, wherein the viral RNA vector comprises a gene-silencing construct.

In a preferred embodiment the kit comprises a viral RNA vector derived from satellite tobacco necrosis vector, preferably comprising the cis-elements required for replication, particularly comprising the nucleotide sequence of SEQ ID No 3 from the nucleotide at position 1 to the nucleotide at position 32 and the nucleotide sequence of SEQ ID No 3 from the nucleotide at position 738 to the nucleotide at position 1245, wherein an origin of assembly of tobacco mosaic virus has been inserted, preferably comprising the nucleotide sequence of SEQ ID No 2 from the nucleotide at position 5443 to the nucleotide at position 5518 or comprising the nucleotide sequence of SEQ ID No 5 from the nucleotide at position 5430 to the nucleotide at position 5505, or comprising the nucleotide sequence of SEQ ID No 12 and wherein said helper virus is derived from tobacco necrosis virus, preferably with a nucleotide sequence of SEQ ID No 1, and comprises a gene encoding the movement protein of tobacco mosaic virus, preferably with the nucleotide sequence of SEQ ID No 2 from the nucleotide at position 4903 to the nucleotide at position 5709 or with the nucleotide sequence of SEQ ID No 15 from the nucleotide at position 479 to the nucleotide at position 1285 and a gene encoding the coat protein of tobacco mosaic virus, preferably with the nucleotide sequence of SEQ ID No 2 from the nucleotide at position 5712 to the nucleotide at position 6191 or with the nucleotide sequence of SEQ ID No 15 from the nucleotide at position 1288 to the nucleotide at position 1767.

Preferred combinations are those kits wherein the viral RNA vector is derived from STNV-1 or STNV-2 strains (as disclosed by Ysebaert et al. 1980; Genbank Accession number M10388 or Danthinne et al., 1991 Genbank Accession M64479) and the helper virus is TNV-A (Meulewaeter et al 1990, SEQ ID No 1). Other preferred combinations are those kits wherein the viral RNA vector is derived from STNV-C (Bringloe et al. (1998); Genbank Accession Nr AJ000898) and the corresponding helper virus is TNV-D (Coutts et al. (1991); Genbank Accession Nr D00942).

In another particularly preferred embodiment the kit comprises a viral RNA vector derived from satellite tobacco mosaic virus, preferably comprising the cis-elements required for replication, particularly comprising the nucleotide sequence of SEQ ID No 4 from the nucleotide at position 1 to the nucleotide at position 197 and the nucleotide sequence of SEQ ID No 4 from the nucleotide at position 604 to the nucleotide at position 1058 or comprising the nucleotide sequence of SEQ ID No 13 and the nucleotide sequence of SEQ ID No 14; and further comprising an origin of assembly of tobacco mosaic virus, preferably comprising the nucleotide sequence of SEQ ID No 2 from the nucleotide at position 5443 to the nucleotide at position 5518 or comprising the nucleotide sequence of SEQ ID No 5 from the nucleotide at position 5430 to the nucleotide at position 5505 or comprising the nucleotide sequence from SEQ ID No 12, and wherein said corresponding helper virus is a tobacco mosaic virus, particularly TMV-U1 (SEQ ID No 2) or TMV-U2 (SEQ ID No 5).

It will be clear to the person skilled in the art that viral RNA vectors may be generated conveniently by in vitro transcription methods from cDNA copies of the viral RNA. Likewise, infectious viral RNA for the corresponding helper viruses may be generated from cDNA copies of their genome. Libraries, viral vectors and corresponding helper viruses may also be maintained by replication in plant cells.

Methods to infect or inoculate plants and plant cells with viral RNA vectors, helper viruses and libraries comprised within viral RNA vectors are well within in the realm of the person skilled in the art and may be performed according to the methods described in Walkey (1985).

In one embodiment of the methods of the invention, plants are inoculated, e.g. with a solution containing the libraries of gene-silencing constructs in a viral vector, or with a solution containing a mixture of gene-silencing constructs in a viral vector and corresponding helper virus. The solution may further contain additional compounds to improve inoculation and infection of the plants, such as, but not limited to abrasives, adherents, tensio-active products and the like.

Plants may be infected during different developmental stages, in order to maximize the phenotype under investigation. Also different parts of plants may be inoculated to optimize observation of the expected phenotype.

Although not intending to limit the scope of the invention to a particular mode of action, it is thought that the inhibitory RNA comprised within the viral RNA vector can exercise its inhibiting effect, provided there is a balance between RNA encapsidated in a virion and free RNA. It is thought that the balance between encapsidated and free RNA may be influenced by varying the sequence and position of an origin of assembly within the viral RNA vector.

However, the gene-silencing effect may be amplified by placing the inhibitory RNA encoding nucleic acid under control of a viral promoter, preferably a coat protein promoter, or a subgenomic promoter so that during the life cycle of the virus additional inhibitory RNA is generated or transcribed.

"Gene-silencing constructs" as used herein is to be interpreted as a nucleic acid, which when transcribed yield "inhibitory RNA" comprising or consisting of sense RNA or antisense RNA, or a combination of both comprising a nucleotide sequence which has at least 75%, preferably at least 80%, particularly at least 85%, more particularly at least 90%, especially at least 95% sequence identity with or is identical to the nucleotide sequence whose expression is to be suppressed, or its complement. Further, the nucleotide sequence of the sense or antisense region should preferably be at least about 100 nucleotides in length, more preferably at least about 250 nucleotides, particularly at least about 500 nucleotides but may extend to the full length of the coding region of the gene whose expression is to be reduced.

For practical purposes in the application of the methods for high throughput screening or validation, the gene-silencing construct may be identical in sequence and length to the target nucleic acids, or they may be exactly complementary in sequence and identical in length to the target nucleic acids.

For the purpose of this invention the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of the two sequences is performed by the Wilbur and Lipmann algorithm (Wilbur and Lipmann, 1983) using a window-size of 20 nucleotides or amino acids, a word length of 2 amino acids, and a gap penalty of 4. Computer-assisted analysis and interpretation of sequence data, including sequence alignment as described above, can be conveniently performed using commercially available software packages such as the programs of the IntelligenetiCS™ Suite (Intelligenetics Inc., CA) or the GCG Wisconsin Package.

It is clear for the person skilled in the art that the gene-silencing constructs may comprise at the same time sense and anti-sense RNA targeted towards the same nucleotide sequence whose expression is to be reduced. Preferably, the sense and antisense RNA are at least partly complementary to each other and capable of forming a stem-loop structure, since such a configuration has been shown to increase the efficiency of gene-silencing, both in occurrence and level of gene-silencing (Waterhouse et al. 1998). In the most straightforward embodiment, at least part of the target nucleic acid, preferably the complete target nucleic acid, is cloned in duplicated form, whereby the two copies are in inverted repeat, preferably separated by an unrelated spacer nucleotide sequence.

The invention also aims at providing the herein described kits in their different embodiments. It is also an object of the invention to provide the kits comprising the helper viruses and viral RNA vectors described without the gene-silencing constructs or inhibitory RNA as well as their cDNA copies, whereby the cDNA copies are under control of a promoter (which can be used in in vitro transcription methods available in the art) such as but not limited to the promoters recognized by single subunit bacteriophage polymerase promoters (T7, T3, SP6 RNA polymerase specific promoters and the like).

The invention further relates to a method for identifying genes which are essential in plants comprising the following steps:

a) A library of random gene-silencing constructs specific for the plant is created using a viral RNA vector which is derived from a satellite RNA virus, as herein defined including all its preferred embodiments. Preferably, the library is created in a cDNA copy of the viral vector and may be generated by inserting random DNA sequences, preferably at least about 100 nucleotides in length, particularly at least about 500 nucleotides in length. The random DNA sequences may be obtained from total DNA of a plant or may represent a subset of the genome of a plant, such as DNA derived from organelles (plastids, chloroplasts, mitochondria etc.) Alternatively, the library may be created by inserting cDNAs generated by reverse transcriptase from RNA, preferably mRNA obtained from said plant. The library may be normalized, e.g. as described in Takayuki et al. (1995). The library should preferably be large enough in size, i.e. contain a sufficient number of independent clones to cover the genome of the plant, according to the standards known in the art. In a preferred embodiment, the library may contain duplication of the inserted nucleic acid whereby the copies are in inverted repeat. The inserted nucleic acid may be cloned downstream of a viral promoter such as, but not limited to a coat protein gene promoter or a subgenomic promoter. It will further be clear to the person skilled in the art that the relative orientation of the inserted nucleic acid, in relation to the RNA vector is only of limited importance since either sense or antisense inhibitory RNA will be generated.

b) Assay plants are infected with individual members of the library and also with a corresponding helper virus. Infection may proceed according to any of the methods mentioned herein. Clearly, the DNA copy of the library should be converted into an RNA copy according to any of the methods described herein, preferably prior to the infection of the assay plants.

c) Plants developing a gene-silencing-construct-associated phenotype are identified. As used herein, a "gene-silencing-construct-associated phenotype" is meant to indicate a phenotype which is not observed when performing a mock inoculation with a viral RNA vector without gene-silencing construct, in combination with a corresponding helper virus on a similar plant. Preferred phenotypes comprise chlorosis, necrosis or any phenotype, preferably a morphological phenotype indicating that the infected tissue is inhibited or dying or deteriorating.

d) Optionally, isolating the viral RNA vector from the tissue exhibiting the gene-silencing-construct-associated phenotype according to methods available in the art for isolation of virus. Preferably, the isolated viral RNA vector comprising the gene-silencing construct of interest should be re-assayed on fresh plants to confirm the observed phenotype. The viral RNA vector can of course also be recovered from the library if the infection of the plants was performed in an identity-preserving way.

e) The gene silencing construct or the nucleotide sequence information thereof, may then be used to recover the corresponding genomic or cDNA clone using methods available in the art (hybridization, PCR etc.)

As defined herein "essential genes" of a plant, are those genes which are necessary during the normal development of a plant. As defined, essential genes may be essential for normal development only in particular developmental stages, or only in particular tissues or organs, such as e.g. flowers. Typically, inhibition of the expression of essential genes may have a lethal effect on a plant or part of a plant. Preferred essential genes are those genes which result in retardation or dying of seedlings when inhibited.

It will be clear for the person skilled in the art that if the inhibition of the target nucleic acid results in a dominant effect, as is the case for inhibition of the expression of essential genes, the described methods may be performed using infection of more than one viral RNA vector comprising a gene-silencing construct per plant. Care has to be taken to not dilute the phenotypic effect too much by infecting a too large number of different viral RNA vectors comprising differing gene-silencing constructs on the same plant. It is thought that optimally any number between one and five different inhibitory RNAs may be introduced in one plant cell.

In yet another embodiment of the invention, a method is provided for determining the function encoded by a nucleic acid comprising a known nucleotide sequence. This nucleotide sequence may have been obtained e.g. from a genome sequencing program, including expressed sequence tags sequencing programs. In order to unravel the function of that sequence, a gene-silencing construct or inhibitory RNA targeted towards said nucleotide sequence, as described in all its embodiments herein, may be introduced into a viral RNA vector derived from a satellite virus, as described herein, and used to inoculate a plant or being introduced into a plant cell, particularly into a protoplast, together with a corresponding helper virus, as described herein.

A large number of the embodiments described herein thus relate to a method for the introduction of inhibitory RNA in plant cells, comprising the steps of:

a.) introducing into a plant cell, a viral RNA vector comprising inhibitory RNA or comprising a chimeric nucleic acid which when transcribed yields the inhibitory RNA, wherein the viral RNA vector is derived from a satellite RNA virus; and b.) introducing into the same plant cell, a corresponding helper virus.

The methods of the invention can be applied to essentially all plants for which viral vector and/or corresponding helper viruses are available. The methods of the invention are thought to be particularly suited for *Nicotiana* spp, particularly *N. tabacum, N. sylvestris, N. benthamiana*, and other Solanaceae, rice (*Oryza sativa*) corn (*Zea mays*), *Brassica* spp., cotton (Gossypum hirsutum), wheat, *Arabidopsis* spp., *Petunia* spp.

Also envisioned by the present invention are methods for developing an agronomically useful product, such as a herbicide or a transgenic plant using the herein described methods and means, further comprising the steps of inserting a nucleic acid, involved in the determination of a particular plant trait, isolated by the methods of the invention, preferably under control of a foreign plant-expressible promoter, particularly under control of a controllable plant-expressible promoter into the genome of a plant, particularly a crop plant. When essential genes have been identified according to the methods described herein, these essential genes or their encoded gene products, particularly the encoded proteins may be used in in vitro assays to identify compounds inhibiting the activity, particularly the enzymatic activity, which may be used as herbicides. Alternatively, a viral RNA vector encoding gene-silencing constructs targeted towards essential genes may be used as herbicidal compounds.

The following non-limiting Examples describe the construction of viral RNA vectors derived from satellite viruses, and uses thereof. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences:

SEQ ID No 1: nucleotide sequence of the genome of TNV-A

SEQ ID No 2: nucleotide sequence of the genome of TMV-U1 (Genbank Accession NrV01408).

SEQ ID No 3: nucleotide sequence of the genome of STNV-2

SEQ ID No 4: nucleotide sequence of the genome of STMV (Genbank accession Nr. M25782).

SEQ ID No 5: nucleotide sequence of the genome of TMV-U2 (Genbank Accession Nr M34077).

SEQ ID No 6: nucleotide sequence of the tomato phytoene desaturase (pds) encoding cDNA (Genbank Accession Nr. X59948).

SEQ ID No 7: nucleotide sequence of the tobacco nitrate reductase (nia-2) encoding cDNA (Genbank Accession Nr. X14059).

SEQ ID No 8: nucleotide sequence of the tobacco nitrite reductase (nir-1) encoding cDNA (Genbank Accession Nr. X66145).

SEQ ID No 9: nucleotide sequence of the β-1,3-glucanase (gn-1) encoding cDNA of *Nicotiana* plumbagenifolia.

SEQ ID No 10: nucleotide sequence of a green fluorescent protein (gfp) encoding region.

SEQ ID No 11: nucleotide sequence of a β-glucuronidase (gus) encoding region.

SEQ ID No 12: nucleotide sequence of an origin of assembly of a TMV-U2 strain.

SEQ ID No 13: nucleotide sequence of the leader sequence of a STMV strain

SEQ ID No 14: nucleotide sequence of the trailer sequence of a STMV strain.

SEQ ID No 15: nucleotide sequence of part of the genome of a TMV-U2 strain comprising movement protein and coat protein genes.

EXAMPLES

Example 1

Construction of the Viral RNA Vector Kits

A plasmid vector for the synthesis of an infective hybrid TMV/TNV helper virus RNA is made using the following operationally linked elements:

A T7 RNA polymerase promoter

A nucleic acid comprising the nucleotide sequence from the nucleotides 1 to 2234 of TNV-A (nt 1 to 2234 of SEQ ID No 1), wherein the AUG codon at nucleotides 2218–2220 mutated to a different codon A nucleic acid comprising the nucleotide sequence encoding the open reading frame for the movement protein of TMV-U1 (nt 4903–5709 of Genbank Accession Number V01408 or nt 4903–5709 of SEQ ID No 2 or nt 479–1285 of SEQ ID No 12)

A nucleic acid comprising the nucleotide sequence from the nucleotides 2235 to 2612 of TNV-A (SEQ ID No 1)

A nucleic acid comprising the nucleotide sequence encoding the open reading frame for the coat protein of TMV-U1 (nt 5712–6191 of Genbank Accession Number V01408 or nt 5712–6191 of SEQ ID No 2 or nt 1288–1767 of SEQ ID No 15)

A sequence comprising nucleotide 3444 to 3684 of TNV-A (nt 3444 to 3684 of SEQ ID No 1)

A plasmid vector for the synthesis of an infective hybrid TMV/STNV viral vector RNA is made using the following operationally linked elements:

A T7 RNA polymerase promoter

A nucleic acid comprising the nucleotide sequence from nucleotide 1 to 32 of STNV-2 (nt 1 to 32 of SEQ ID No 3)

A nucleic acid comprising the origin of assembly (OAS) of TMV-U1 (nt. 5443–5518 of Genbank Accession Number V01408 or nt 5443–5518 of SEQ ID No 2 or nt 1018 to 1094 of SEQ ID No 15)

A nucleic acid comprising the nucleotide sequence from nucleotide 738 to 1245 of STNV-2 (nt 738 to 1245 of SEQ ID No 3)

A plasmid vector for the synthesis of an infective hybrid TMV/STMV viral vector RNA is made using the following operationally linked elements:

A T7 RNA polymerase promoter

A nucleic acid comprising the nucleotide sequence from nucleotide 1 to 197 of STMV (Genbank Accession Number M25782; nt 1 to 197 of SEQ ID No 4) or the nucleotide sequence of SEQ ID No 13.

A nucleic acid comprising the OAS of TMV-U1 (nt. 5443–5518 of Genbank Accession Number V01408; nt 5443 to 5518 of SEQ ID No 2; nt 1019–1094 of SEQ ID No 15) or of TMV-U2 (nt 5430–5505 of Genbank Accession Number M34077; nt 5430–5505 of SEQ ID No 5) such as the nucleotide sequence of SEQ ID No 12.

A nucleic acid comprising the nucleotide sequence from nucleotide 604 to 1058 of STMV (Genbank Accession Number M25782; nt 604 to 1058 of SEQ ID No 4) or comprising the nucleotide sequence of SEQ ID No 14.

Example 2

Feasibility Demonstration Using Known Endogenes or Transgenes

To demonstrate the feasibility of the use of the viral kits described sub example 1 for functional knockout of specific endo- or transgenes in *Nicotiana* plants, one of the following DNA fragments is inserted in the TMV/STNV or TMV/STMV hybrid vector, immediately upstream or downstream of the TMV OAS:

a fragment of the tomato pythoene desaturase (pds) cDNA (comprising nucleotide 1021 to 1671 of SEQ ID No 6 or Genbank Accession Number X59948)

a fragment of the tobacco nitrate reductase (nia-2) cDNA (comprising nucleotides 1103 to 2114 or nucleotides 5169 to 6497 of SEQ ID No 7 or Genbank Accession Number X14059)

a fragment of the tobacco nitrite reductase (nir-1) cDNA (comprising nucleotide 650–1212 of SEQ ID No 8 or Genbank Accession Number X66145)

a fragment of the β-1,3-glucanase (gn-1) cDNA of *Nicotiana* plumbaginifolia (SEQ ID No 9 or Genbank Accession Number X07280)

a fragment comprising a nucleotide sequence from a green fluorescent protein (gfp) coding region (SEQ ID No 10)

a fragment comprising a nucleotide sequence from nucleotide 1 to 600 of the β-glucuronidase (gus) coding region (SEQ ID No 11)

Infective chimeric transcripts are synthesized in vitro, using T7 RNA polymerase with the linearized plasmid DNAs of the described vectors as templates. The TMV/STNV RNAs are mechanically inoculated on leaves of *Nicotiana benthamiana* or *Nicotiana tabacum* plants together with the TMV/TNV RNA, whereas the TMV/STMV RNAs are inoculated together with TMV-U2 virus particles or viral RNA.

The infected plants are scored for phenotypes, virus accumulation, and suppression of the homologous plant gene between 1 and 4 weeks after inoculation.

Plants infected with vectors containing the pds cDNA show a bleaching phenotype on infected leaves and silencing of the endogenous pds transcript. Plants infected with vectors containing the nia-2 or nir-1 cDNA show a chlorotic phenotype on infected leaves and silencing of the endogenous nia-2 or nir-1 transcript, respectively.

Plants infected with vectors containing the gn-1 cDNA show silencing of the endogenous basic -1,3-glucanase transcript.

Upon infection with vectors containing the gfp sequence, transgenic plants that normally express a gfp transgene show silencing of the gfp transgene transcript and suppression of GFP fluorescence.

Upon infection with vectors containing the gus sequence, transgenic plants that normally express a gus transgene show silencing of the gus transgene transcript and suppression of GUS activity.

Example 3

Inactivation of Phytoene Desaturase in *Nicotiana Benthamiana* Using a TNV/STNV Hybrid Vector System A TNV/STNV hybrid vector system was used for the functional inactivation of a constitutively expressed endogenous plant gene. Therefore, the following STNV hybrid vectors have been constructed:

plF9 carrying the following operationally linked elements:

a T7 RNA polymerase promoter comprising nucleotide 402 to 420 of Genbank Accession Number M77811;

a nucleic acid comprising the nucleotide sequence from nucleotide 1 to 32 of SEQ ID No 3 (STNV-2 leader);

a nucleic acid comprising the origin of assembly (OAS) of TMV-U1 from nucleotide 5443 to 5518 of SEQ ID No 2 or Genbank Accession Number V01408;

a fragment of the tomato phytoene desaturase (pds) cDNA comprising nucleotide 1021 to 1671 of SEQ ID No 6 or Genbank Accession Number X59948;

a nucleic acid comprising the nucleotide sequence from nucleotide 806 to 1418 of SEQ ID No 3 (STNV-2 trailer).

plF12 carrying the following operationally linked elements:

a T7 RNA polymerase promoter comprising nucleotide 402 to 420 of Genbank Accession Number M77811;

a nucleic acid comprising the nucleotide sequence from nucleotide 1 to 32 of SEQ ID No 3 (STNV-2 leader);

a fragment of the tomato phytoene desaturase (pds) cDNA comprising nucleotide 1021 to 1671 of SEQ ID No 6 or Genbank Accession Number X59948;

a nucleic acid comprising the nucleotide sequence from nucleotide 742 to 1354 of SEQ ID No 3 (STNV-2 trailer).

Infective chimeric transcripts have been synthesized in vitro using T7 RNA polymerase with the linearized plasmid DNAs of the described plF9 and plF12 hybrid vectors as templates using standard procedures. Control in vitro transcripts have been synthesized on linearized plasmid DNAs of the precursor plasmids of plF9 and plF12 without the pds fragment inserts and on linearized plasmid DNA of an infective clone of the STNV wild type and of a hybrid STNV vector carrying an insert of the cat gene.

The in-vitro transcripts have been mechanically inoculated onto leaves of four weeks old *Nicotiana benthamiana* plants together with the TNV helper virus.

All infected plants were continuously scored for pds inactivation, which resulted in a phenotype showing leaf bleaching. For all inoculations necrotic lesions were observed for the inoculated leaves after 2 days post inoculation (p.i.). Within a week, necrotic lesions also occurred in upper leaves indicating the systemic spread of the viruses in N.benthamiana. In most infected plants, the virus symptoms have been severe but plants survived for many weeks.

Only plants, which have been infected with the hybrid vectors plF9 and plF12 carrying pds fragments, showed on top of the virus symptoms additional phenotypic changes. Approximately 4 weeks p.i., green upper leaves, which did not show any virus symptoms, developed bleached spots scattered all over the leaves. The bleaching was progressive and was not accompanied by necrotic lesions. Within another three weeks, the size of the spots increased constantly and the color changed from pale green to yellow to pale white-yellow. These symptoms have never been observed in plants, on which TNV/STNV wild type or TNV/STNV-deletion mutant control inoculations were carried out. Thus, this phenotype indicates the functional knockout of pds in *N. benthamiana* plants after infection with plF9 and plF12 hybrid viral vectors.

In RNA gel blot analyses performed with total RNA preparations of green and bleached spots of upper leaves of plants showing a FKO phenotype no chimeric STNV virus RNA and only very low levels of TNV helper virus RNA could be detected. This indicates that virus induced gene silencing of pds in a specific tissue does not need to be accompanied by high levels of virus RNA.

Example 4

Inactivation of Phytoene Desaturase in *Petunia Hybrida* Using a TMV/STMV Hybrid Vector System A TMV/STMV hybrid vector system was used for the functional inactivation of a constitutively expressed endogenous plant gene. Therefore, the following STMV hybrid vectors have been constructed:

pVE293 carrying the following operationally linked elements:

- a T7 RNA polymerase promoter comprising nucleotide 402 to 420 of Genbank Accession Number M77811
- a nucleic acid comprising the nucleotide sequence from nucleotide 1 to 197 of STMV of SEQ ID No 4 or Genbank Accession Number M25782 (STMV leader)
- a nucleic acid comprising the origin of assembly (OAS) of TMV-U2 from nucleotide 5430 to 5505 of SEQ ID No 5 or Genbank Accession Number M34077 (“short” TMV OAS)
- a fragment of the tomato phytoene desaturase (pds) cDNA comprising nucleotide 1021 to 1671 of SEQ ID No 6 or Genbank Accession Number X59948
- a nucleic acid comprising the nucleotide sequence from nucleotide 604 to 1058 of STMV of SEQ ID No 4 or Genbank Accesion Number M25782 (STMV trailer)
- a SP6 RNA polymerase promoter comprising nucleotide 143 to 124 of Genbank Accession Number X65308 pVE294 carrying the following operationally linked elements:

- a T7 RNA polymerase promoter comprising nucleotide 402 to 420 of Genbank Accession Number M77811
- a nucleic acid comprising the nucleotide sequence from nucleotide 1 to 197 of STMV of SEQ ID No 4 or Genbank Accession Number M25782 (STMV leader)
- a nucleic acid comprising the origin of assembly (OAS) of TMV-U2 from nucleotide 5441 to 5849 of SEQ ID No 2 or Genbank Accession Number M34077 (“long” TMV OAS)
- a fragment of the tomato phytoene desaturase (pds) cDNA comprising nucleotide 1021 to 1671 of SEQ ID No 6 or Genbank Accession Number X59948
- a nucleic acid comprising the nucleotide sequence from nucleotide 604 to 1058 of STMV of SEQ ID No 4 or Genbank Accesion Number M25782 (STMV trailer)
- a SP6 RNA polymerase promoter comprising nucleotide 143 to 124 of Genbank Accession Number X65308

Infective chimeric transcripts have been synthesized in vitro using T7 RNA polymerase with the linearized plasmid DNAs of the described pVE293 and pVE294 hybrid vectors as templates using standard procedures. Control in vitro transcripts have been synthesized on linearized plasmid DNAs of the precursor plasmids of pVE293 and pVE294 without the pds fragment insert and on linearized plasmid DNA of the infective clone STMV-10 of the wild type.

The in vitro transcripts have been mechanically inoculated onto leaves of three months old *Petunia hybrida* V26 plants together with the TMV-U2 helper virus.

The infected plants have been continuously scored for pds inactivation, which resulted in a phenotype showing leaf bleaching. The infection of petunia plants with TMV/STMV caused the occurrence of crinkled leaves starting from the infected branches but quickly progressing systemically throughout the plant. The plants did survive the infections and often showed recovery phenotypes with almost no symptoms.

Only the plants, which have been infected with the hybrid vectors pVE293 and pVE294 carrying the pds fragment, showed in addition to the virus symptoms, additional phenotypic changes. In case of TMV/pVE293 infections, the infected branches developed young leaves with bleached sectors around the veins and at the tip of the leaves. This bleaching was progressive and independent from the presence of virus symptoms. Some of the leaves were fully bleached and progressively changed into almost white color. This phenotype was restricted to leaves of the infected branches. In case of TMV/pVE294 infections a similar bleaching of young leaves was observed for all developing branches but not for branches carrying already terminal flower buds. The bleaching started again around the veins and leaf tips but proceeded quickly producing variable leaf variegation patterns. This phenotype has never been observed in control inoculations with wild type viruses or deletion mutants. Therefore this phenotype indicates the functional knockout of pds in *Petunia hybrida* plants after infection with pVE293 and pVE294 viral hybrid vectors.

In RNA gel blot analyses performed with total RNA preparations of green and bleached spots of upper leaves of plants showing a FKO phenotype no chimeric STMV virus RNA and only low levels of TMV helper virus RNA could be detected. This indicates that virus induced gene silencing of pds in a specific tissue does not need to be accompanied by high levels of virus RNA.

REFERENCES

Ausubel et al. (1994) *Current Protocols in Molecular Biology, Current Protocols*, USA.

Baulcombe (1996) Plant Cell 8: 1833–1844

Baulcombe et al. (1998) JIC &SL Annual Report 1996/1997

Bringloe et al. (1998) 79: 1539–1546

Chapman (1991) PhD dissertation, University of Cambridge, UK

Coutts et al. (1991) J. Gen. Virology 72: 1521–1529

Danthinne et al. (1991) Virology 185: 605–614

Depicker and Van Montagu (1997) Curr. Opin. Cell. Biol. 9: 373–382

English et al. (1996) Plant Cell 8,179–188

Hamilton et al. (1998) The Plant Journal 15(6): 737–746

Kempin et al. (1997) Nature 389: 802–803

Kumagai et al. (1995) Proc. Natl. Acad. Sci USA 92: 1679–1683

Meulewaeter et al (1990) Virology 177:699–709

Pereira and Aerts (1998) Methods in Molecular Biology 82 Eds. Martinez-Zapatar and Salinas, Humana Press, N.J.

R. D. D. Croy (1993) Plant Molecular Biology Labfax jointly published by BIOS Scientific Publications Ltd (UK) and Blackwell Scientific Publications, UK.

Prahasar et al. (1996) Proc. Natl. Acad. Sci USA 93: 659–663

Ruiz et al. (1998) The Plant Cell 10: 937–946

Sambrook et al. (1989) Molecular Cloning: A Laboratory Manual, Second Edition, Cold Spring Harbor Laboratory Press, NY Stam et al. (1997) Ann. Botan. 79:3–12

Takayuki et al. (1995) The Plant Journal 8(5):771–776

Walkey (1985) Applied Virology, William Heinemann Ltd, London

Waterhouse et al. (1998) Proc. Natl. Acad. Sci USA 95: 13959–13964

Wellink et al. (1998) Abstract presented at the Joint Meeting of Arbeitskreis Virologie and Nederlandse Kring voor Plantenvirologie in Wageningen, The Netherlands, Nov. 12 and 13, 1998.

Wilbur and Lipmann (1983) Proc. Nat. Acad. Sci. USA 80: 726

Ysebaert et al. (1980) J. Mol. Biol. 143: 273–287

SEQUENCE LISTING

```
<160> NUMBER OF SEQ ID NOS: 15

<210> SEQ ID NO 1
<211> LENGTH: 3684
<212> TYPE: DNA
<213> ORGANISM: Artificial Sequence
<220> FEATURE:
<223> OTHER INFORMATION: Description of Artificial Sequence:cDNA copy of
      the nucleotide sequence of the genome of TNV-A

<400> SEQUENCE: 1

agtattcata ccaagaatac caaataggtg caaggcctta ctcagctaaa gagtctaaaa     60

tggagctacc aaaccaacac aagcaaacgg ccgccgaggg tttcgtatct ttcctaaact    120

ggctatgcaa cccatggaga cgacagcgaa cagtcaacgc tgcagttgcg ttccaaaaag    180

atcttctcgc cattgaggat tccgagcatt tggatgacat caatgagtgt ttcgaggagt    240

ctgctggggc acaatctcag cgaactaagg ttgtcgccga cggagcatat gccccgcaa     300

aatccaacag gacccgccga gttcgtaagc agaagaagca caagtttgta aaatatcttg    360

tcaacgaagc tcgtgccgag tttggattgc ccaaaccaac tgaggcaaac agacttatgg    420

tccaacattt cttgctcaga gtgtgcaagg attggggcgt tgttactgcc cacgtacacg    480

gcaatgttgc actagctttg ccactggtgt tcatcccaac ggaagatgat ctgctatcac    540

gagcattgat gaacacacat gctactagag ccgctgtacg aggcatggac aatgtccaag    600

gggaggggtg gtggaacaat aggttgggga ttgggggcca ggtcggactg gccttccggt    660

ccaaataggg gtgccttgaa aggaggccag gattctccac gtccgtttcg cgtggggaac    720

atcctgatct ggtggtcata ccatcagggc gccctgagaa acagcgtcag ttgttacgct    780

atagtggtat aggcggccat ttattaatcg gcatccacaa caactctctt tccaacctgc    840

gtaggggctt gatggaaaga gtattctatg tcgagggggcc caatgggctt caagacgccc   900

ctaagcccgt caagggagct tttcgaaccc ttgataagtt tcgtgatctc tatactaaaa    960

atagttggcg tcataccccct gtaactagtg aacaattcct aatgaattac acgggcagga  1020

aactgactat ttacagagag gcggttgata gtttgtcgca tcaacccctt agctcacgag   1080
```

-continued

```
atgcgaaact aaagacattc gtgaaggccg aaaaattaaa tctttctaag aagcctgacc   1140
ctgctcccag ggtcatccaa cctagatcgc ctcggtataa cgtttgtttg ggcaggtacc   1200
tccgacatta tgagcatcac gcgtttaaaa ccattgccaa gtgctttggg gaaatcacgg   1260
tcttcaaagg gtttactctg gagcaacaag gggaaatcat gcgctcgaag tggaataaat   1320
atgttaatcc cgtcgcagtc ggactcgacg ccagtcgttt cgaccaacac gtgtctgttg   1380
aagcactcga gtatgagcat gaattttacc tcagagacta cccaaatgat aaacagctaa   1440
aatggctgct aaagcagcaa ttgtgcaacg taggaacggc attcgccagt gacggcatta   1500
taaaatacaa gaagaagggt tgtagaatga gcggagacat gaacacgagt ttgggcaact   1560
gcattctaat gtgcgccatg gtctacgggt tgaaagaaca cttaaacatc aatttgtccc   1620
ttgcaaataa tggggatgac tgcgtcattg tctgtgagaa agcggattta aagaaattga   1680
caagcagcat cgagccatat ttcaagcagt ttggattcaa gatggaagtg gaaaaacccg   1740
tggatatatt tgagcgcata gaattttgcc aaacccaacc tgtgttcgat ggatcccagt   1800
acatcatggt acgcaaacct tctgtggtaa catctaaaga cgtcactagc cttatcccat   1860
gtcaaacgaa agcacaatac gcagaatggc tgcaagctgt aggtgagtgt ggcatgagca   1920
ttaacggtgg gattcctgtc atgcagaatt tctaccaaaa gctccaaact ggcatccgcc   1980
gcacaaaatt caccaagacc ggcgagttcc agacgaacgg attggggtat cactctagat   2040
atatgcatag agtggcccgg gttccttcgc ctgaaacccg tttatccttc tatctagctt   2100
tcggtatcac accagacctc caagaagcat tggagatctt ctatgatacc cacaggcttg   2160
agttggatga tgttatccca actgatacct accaagtgtc aggagagcat ttgatcaatg   2220
gattaccaaa ctgatgtaac ggaggacaat gtgcaaatac gcggtcgggc taggagcgtt   2280
gagggtaaga aacacaatgg ttcgggatta actggcgtta agcgtcacgc ggtgagcgaa   2340
acatctcaga aatcacagca aggtactggc aatggaacta tgaccaatat agccgaagaa   2400
cagaccatta ccgtgacata caactttaac ttttaagtta tggctgcgtg tcgctgttgt   2460
gatacttcac caggtattac actattccct tactttgcaa ttctcatcct tatattggca   2520
atacttgttg tagggactcc caatcaacaa tatcaccatt ctccaagcac ttacgagtac   2580
aagactcaac acatttcgat cgcaaaatag acatggcagg aaagaagaac aacaacaacg   2640
gtcagtatat aatactgcgt actccagagc aacaggtgga gatagaccag cgcaacgccc   2700
gtcgtgctca aatgggtcgc atgaagaagg ctagacagcc cgttcagcga tacttacagc   2760
aacacgggtt gcgaaacgga ttgtccggta gaggggggcta catagtggct cccacctccg   2820
ggggggttgt cactcgaccc atagtgccga aattctccaa caggggagat tccactatag   2880
tccgtaacac tgagattttg aacaaccaaa tcttagcggc gctaggcgca ttcaatacaa   2940
caaactccgc actgattgca gcagcaccat catggctggc tagcatcgct gatctttaca   3000
gtaaatacag atggctctca tgtgagatca tctacattcc aaaatgcccc accaccacca   3060
gtggatcaat tgccatggct ttcacatacg acagaaatga cgctgcaccc accgcaaggg   3120
ctcagctgtc acaatcttac aaggccatca attttccacc gtatgcggga tacgacggag   3180
cagcatattt gaattcgaac cagggagctg ggtcagccat cgccgttcaa cttgatgtta   3240
ccaagttgga caagccatgg taccccacta tctcctctgc cggcttcggg gcgctcagcg   3300
tcctcgatca gaaccaattc tgccccgcgt cccttgtggt cgctagcgat gggggacccg   3360
ctactgctac tccagcaggg gaccttttca tcaagtacgt gattgagttc attgaaccaa   3420
```

-continued

```
tcaacccaac aatgaacgtc tagttctttg tactgtaact tggctaatgc ctaaggtgga   3480

gtcacaccat tggagacgga gacggatcct gggaaacagg cttgacgggc ggggggtggt   3540

gcccccgacg acgcatcact ccggatacca atggtacacc actatggcag ggtctgccaa   3600

ggtcttgtgc accaagaacc cctggaaacg ggggggaggg gggtagcaca tatcatccag   3660

attgaggggc ctttgcccca cccc                                          3684


<210> SEQ ID NO 2
<211> LENGTH: 6395
<212> TYPE: DNA
<213> ORGANISM: Artificial Sequence
<220> FEATURE:
<223> OTHER INFORMATION: Description of Artificial Sequence: cDNA copy
      of the nucleotide sequence of the genome of TMV-U1

<400> SEQUENCE: 2

gtatttttac aacaattacc aacaacaaca aacaacaaac aacattacaa ttactattta     60

caattacaat ggcatacaca cagacagcta ccacatcagc tttgctggac actgtccgag    120

gaaacaactc cttggtcaat gatctagcaa agcgtcgtct ttacgacaca gcggttgaag    180

agtttaacgc tcgtgaccgc aggcccaagg tgaacttttc aaaagtaata agcgaggagc    240

agacgcttat tgctacccgg gcgtatccag aattccaaat tacattttat aacacgcaaa    300

atgccgtgca ttcgcttgca ggtggattgc gatctttaga actggaatat ctgatgatgc    360

aaattcccta cggatcattg acttatgaca taggcgggaa ttttgcatcg catctgttca    420

agggacgagc atatgtacac tgctgcatgc ccaacctgga cgttcgagac atcatgcggc    480

acgaaggcca gaaagacagt attgaactat acctttctag gctagagaga gggggggaaaa    540

cagtccccaa cttccaaaag gaagcatttg acagatacgc agaaattcct gaagacgctg    600

tctgtcacaa tactttccag acaatgcgac atcagccgat gcagcaatca ggcagagtgt    660

atgccattgc gctacacagc atatatgaca taccagccga tgagttcggg gcggcactct    720

tgaggaaaaa tgtccatacg tgctatgccg ctttccactt ctctgagaac ctgcttcttg    780

aagattcata cgtcaatttg gacgaaatca acgcgtgttt ttcgcgcgat ggagacaagt    840

tgaccttttc ttttgcatca gagagtactc ttaattattg tcatagttat tctaatattc    900

ttaagtatgt gtgcaaaact tacttcccgg cctctaatag agaggtttac atgaaggagt    960

tttagtcac cagagttaat acctggtttt gtaagttttc tagaatagat acttttcttt   1020

tgtacaaagg tgtggcccat aaaagtgtag atagtgagca gttttatact gcaatggaag   1080

acgcatggca ttacaaaaag actcttgcaa tgtgcaacag cgagagaatc ctccttgagg   1140

attcatcatc agtcaattac tggtttccca aaatgaggga tatggtcatc gtaccattat   1200

tcgacatttc tttggagact agtaagagga cgcgcaagga agtcttagtg tccaaggatt   1260

tcgtgtttac agtgcttaac cacattcgaa cataccaggc gaaagctctt acatacgcaa   1320

atgttttgtc ctttgtcgaa tcgattcgat cgagggtaat cattaacggt gtgacagcga   1380

ggtccgaatg ggatgtggac aaatctttgt tacaatcctt gtccatgacg ttttacctgc   1440

atactaagct tgccgttcta aaggatgact tactgattag caagtttagt ctcggttcga   1500

aaacggtgtg ccagcatgtg tgggatgaga tttcgctggc gtttgggaac gcatttccct   1560

ccgtgaaaga gaggctcttg aacaggaaac ttatcagagt ggcaggcgac gcattagaga   1620

tcagggtgcc tgatctatat gtgaccttcc acgacagatt agtgactgag tacaaggcct   1680

ctgtggacat gcctgcgctt gacattagga agaagatgga agaaacggaa gtgatgtaca   1740
```

-continued

```
atgcactttc agagttatcg gtgttaaggg agtctgacaa attcgatgtt gatgtttttt   1800
cccagatgtg ccaatctttg gaagttgacc caatgacggc agcgaaggtt atagtcgcgg   1860
tcatgagcaa tgagagcggt ctgactctca catttgaacg acctactgag gcgaatgttg   1920
cgctagcttt acaggatcaa gagaaggctt cagaaggtgc tttggtagtt acctcaagag   1980
aagttgaaga accgtccatg aagggttcga tggccagagg agagttacaa ttagctggtc   2040
ttgctggaga tcatccggag tcgtcctatt ctaagaacga ggagatagag tctttagagc   2100
agtttcatat ggcaacggca gattcgttaa ttcgtaagca gatgagctcg attgtgtaca   2160
cgggtccgat taaagttcag caaatgaaaa actttatcga tagcctggta gcatcactat   2220
ctgctgcggt gtcgaatctc gtcaagatcc tcaaagatac agctgctatt gaccttgaaa   2280
cccgtcaaaa gtttggagtc ttggatgttg catctaggaa gtggttaatc aaaccaacgg   2340
ccaagagtca tgcatggggt gttgttgaaa cccacgcgag gaagtatcat gtggcgcttt   2400
tggaatatga tgagcagggt gtggtgacat gcgatgattg gagaagagta gctgtcagct   2460
ctgagtctgt tgtttattcc gacatggcga aactcagaac tctgcgcaga ctgcttcgaa   2520
acggagaacc gcatgtcagt agcgcaaagg ttgttcttgt ggacggagtt ccgggctgtg   2580
ggaaaaccaa agaaattctt tccagggtta attttgatga agatctaatt ttagtacctg   2640
ggaagcaagc cgcggaaatg atcagaagac gtgcgaattc ctcagggatt attgtggcca   2700
cgaaggacaa cgttaaaacc gttgattctt tcatgatgaa ttttgggaaa agcacacgct   2760
gtcagttcaa gaggttattc attgatgaag ggttgatgtt gcatactggt tgtgttaatt   2820
ttcttgtggc gatgtcattg tgcgaaattg catatgttta cggagacaca cagcagattc   2880
catacatcaa tagagtttca ggattcccgt accccgccca ttttgccaaa ttggaagttg   2940
acgaggtgga gacacgcaga actactctcc gttgtccagc cgatgtcaca cattatctga   3000
acaggagata tgagggcttt gtcatgagca cttcttcggt taaaaagtct gtttcgcagg   3060
agatggtcgg cggagccgcc gtgatcaatc cgatctcaaa acccttgcat ggcaagatcc   3120
tgacttttac ccaatcggat aaagaagctc tgctttcaag agggtattca gatgttcaca   3180
ctgtgcatga agtgcaaggc gagacatact ctgatgtttc actagttagg ttaacccta    3240
caccagtctc catcattgca ggagacagcc cacatgtttt ggtcgcattg tcaaggcaca   3300
cctgttcgct caagtactac actgttgtta tggatccttt agttagtatc attagagatc   3360
tagagaaact tagctcgtac ttgttagata tgtataaggt cgatgcagga acacaatagc   3420
aattacagat tgactcggtg ttcaaaggtt ccaatctttt tgttgcagcg ccaaagactg   3480
gtgatatttc tgatatgcag ttttactatg ataagtgtct cccaggcaac agcaccatga   3540
tgaataattt tgatgctgtt accatgaggt tgactgacat ttcattgaat gtcaaagatt   3600
gcatattgga tatgtctaag tctgttgctg cgcctaagga tcaaatcaaa ccactaatac   3660
ctatggtacg aacggcggca gaaatgccac gccagactgg actattggaa aatttagtgg   3720
cgatgattaa aaggaacttt aacgcacccg agttgtctgg catcattgat attgaaaata   3780
ctgcatcttt agttgtagat aagttttttg atagttattt gcttaaagaa aaaagaaaac   3840
caaataaaaa tgtttctttg ttcagtagag agtctctcaa tagatggtta gaaaagcagg   3900
aacaggtaac aataggccag ctcgcagatt ttgattttgt agatttgcca gcagttgatc   3960
agtacagaca catgattaaa gcacaaccca agcaaaaatt ggacacttca atccaaacgg   4020
agtacccggc tttgcagacg attgtgtacc attcaaaaaa gatcaatgca atatttggcc   4080
cgttgtttag tgagcttact aggcaattac tggacagtgt tgattcgagc agatttttgt   4140
```

-continued

```
ttttcacaag aaagacacca gcgcagattg aggatttctt cggagatctc gacagtcatg   4200
tgccgatgga tgtcttggag ctggatatat caaaatacga caaatctcag aatgaattcc   4260
actgtgcagt agaatacgag atctggcgaa gattgggttt tgaagacttc ttgggagaag   4320
tttggaaaca agggcataga aagaccaccc tcaaggatta taccgcaggt ataaaaactt   4380
gcatctggta tcaaagaaag agcgggggacg tcacgacgtt cattggaaac actgtgatca   4440
ttgctgcatg tttggcctcg atgcttccga tggagaaaat aatcaaagga gccttttgcg   4500
gtgacgatag tctgctgtac tttccaaagg gttgtgagtt tccggatgtg caacactccg   4560
cgaatcttat gtggaatttt gaagcaaaac tgtttaaaaa acagtatgga tacttttgcg   4620
gaagatatgt aatacatcac gacagaggat gcattgtgta ttacgatccc ctaaagttga   4680
tctcgaaact tggtgctaaa cacatcaagg attgggaaca cttggaggag ttcagaaggt   4740
ctctttgtga tgttgctgtt tcgttgaaca attgtgcgta ttacacacag ttggacgacg   4800
ctgtatggga ggttcataag accgcccctc caggttcgtt tgtttataaa agtctggtga   4860
agtatttgtc tgataaagtt ctttttagaa gtttgtttat agatggctct agttgttaaa   4920
ggaaaagtga atatcaatga gtttatcgac ctgacaaaaa tggagaagat cttaccgtcg   4980
atgtttaccc ctgtaaagag tgttatgtgt tccaaagttg ataaaataat ggttcatgag   5040
aatgagtcat tgtcagaggt gaaccttctt aaaggagtta agcttattga tagtggatac   5100
gtctgtttag ccggtttggt cgtcacgggc gagtggaact tgcctgacaa ttgcagagga   5160
ggtgtgagcg tgtgtctggt ggacaaaagg atggaaagag ccgacgaggc cactctcgga   5220
tcttactaca cagcagctgc aaagaaaaga tttcagttca aggtcgttcc caattatgct   5280
ataaccaccc aggacgcgat gaaaaacgtc tggcaagttt tagttaatat tagaaatgtg   5340
aagatgtcag cgggtttctg tccgctttct ctggagtttg tgtcggtgtg tattgtttat   5400
agaaataata taaaattagg tttgagagag aagattacaa acgtgagaga cggagggccc   5460
atggaactta cagaagaagt cgttgatgag ttcatggaag atgtccctat gtcgatcagg   5520
cttgcaaagt ttcgatctcg aaccggaaaa aagagtgatg tccgcaaagg gaaaaatagt   5580
agtaatgatc ggtcagtgcc gaacaagaac tatagaaatg ttaaggattt tggaggaatg   5640
agttttaaaa agaataattt aatcgatgat gattcggagg ctactgtcgc cgaatcggat   5700
tcgttttaaa tatgtcttac agtatcacta ctccatctca gttcgtgttc ttgtcatcag   5760
cgtgggccga cccaatagag ttaattaatt tatgtactaa tgccttagga aatcagtttc   5820
aaacacaaca agctcgaact gtcgttcaaa gacaattcag tgaggtgtgg aaaccttcac   5880
cacaagtaac tgttaggttc cctgacagtg actttaaggt gtacaggtac aatgcggtat   5940
tagacccgct agtcacagca ctgttaggtg cattcgacac tagaaataga ataatagaag   6000
ttgaaaatca ggcgaacccc acgactgccg aaacgttaga tgctactcgt agagtagacg   6060
acgcaacggt ggccataagg agcgcgataa ataatttaat agtagaattg atcagaggaa   6120
ccggatctta taatcggagc tctttcgaga gctcttctgg tttggtttgg acctctggtc   6180
ctgcaacttg aggtagtcaa gatgcataat aaataacgga ttgtgtccgt aatcacacgt   6240
ggtgcgtacg ataacgcata gtgtttttcc ctccacttaa atcgaagggt tgtgtcttgg   6300
atcgcgcggg tcaaatgtat atggttcata tacatccgca ggcacgtaat aaagcgaggg   6360
gttcgaatcc ccccgttacc cccggtaggg gccca                                6395
```

<210> SEQ ID NO 3

-continued

<211> LENGTH: 1245
<212> TYPE: DNA
<213> ORGANISM: Artificial Sequence
<220> FEATURE:
<223> OTHER INFORMATION: Description of Artificial Sequence: cDNA copy of the nucleotide sequence of the genome of STNV-2

<400> SEQUENCE: 3

```
agtaaagaca ggaaacttta ccgactatca gaatgacaaa acgtcaaagc aaacaatcaa     60

accgcaagag cgttgcatca caggtgcgta gtattgttga gtcaatggct gagcagaagc    120

gatttgcttt tcttacgaac accaacacag tcactacagc aggtaccgtg atcaacctga    180

gcaacaacat cgtgcaagga gatgaccttg ttaatcgcac cggagaccag attaagacca    240

tacaccagac tttattgact cggtgtacag gaattaccaa cagccaaagc tttcggttca    300

tctggtttcg tgacaacacc aataggggga ctacaccggc tgtgactgag gtgttagaca    360

gtgctagtat aacatcccag tataacccca ctacgttcca gcaaaagagg ttcactgttt    420

tccaagattt catgttggat acctctatag ttggacgtgt gattgtccat cggactgccg    480

ttgataagaa acggcgtgcg atattttaca acggtgctgc ttctgtagcc gcgtcaaatg    540

gccccggtgc cacatttgta cttgtcattg gatcacatgc cactggacag tatgatgtga    600

cagccgagat tgtttatctg gacatgtaga ccatggtcat gatgatgata gtgaaggacg    660

ctgaaagatg cgtagctacc ctcctggtgc acttcctggt gcaaagcaga accaaagggt    720

acggtggtac ggcggacagt agtcctgaac tagtaaatca ggaccgggag aaaaccagct    780

gacggctaaa tccattccca ctagtgtatt agtggaacga ggccccgcgt gaattggggt    840

ggctgcatgg ggtggaaaac catgtggtcg cagtcatttc tcctatgcat tattgtctca    900

atacttgtgt gcaacaatgc tgttaatcaa cgtagcactc aacatcactt caaaaccccc    960

tccatgtcac aagaatcaag atgcatgtct gtgtttagcg gtatatattt tgcatccact   1020

tgatcgtgat tttgccctgg gcacctcgcg cggttggtac ccgcggagac tccccacagc   1080

aacatggcat taggcaggga taaggtatag tgactagaca aatgcgcgtg aagctggaaa   1140

gtccggttag cagtggggtt gtgcggaatg cagcctcaac aaggtatagc tgctgcatag   1200

gagatgtgaa cctttcaaac ttgaattcaa gtctcatgac tgccc                   1245
```

<210> SEQ ID NO 4
<211> LENGTH: 1058
<212> TYPE: DNA
<213> ORGANISM: Artificial Sequence
<220> FEATURE:
<223> OTHER INFORMATION: Description of Artificial Sequence: cDNA copy of the nucleotide sequence of the genome of STMV

<400> SEQUENCE: 4

```
agtaaactta ccaatcaaaa gacctaacca acaggactgt cgtggtcatt tatgctgttg     60

ggggacatag ggggaaaaca tattgccttc ttctacaaga ggccttcagt cgccataatt    120

acttggcgcc caattttggg tttcagttgc tgtttccagc tatgggggaga ggtaaggtta    180

aaccaaaccg taaatcgacg ggtgacaatt cgaatgttgt tactatgatt agagctggaa    240

gctatcctaa ggtcaatccg actccaacgt gggtcagagc catacctttc gaagtgtcag    300

ttcaatctgg tattgctttt aaagtaccgg tcgggtcact attttcggca aatttccgga    360

cagattcctt tacaagcgtc acagtgatga gtgtccgtgc ttggacccag ttaacaccgc    420

cagtaaatga gtacagtttt gtgaggctga agccattgtt caagactggt gactctactg    480

aggagttcga agggcgtgca tcaaacatca acacacgagc ttctgtaggg tacaggattc    540
```

-continued

```
caactaattt gcgtcagaat actgtggcag ccgacaatgt atgcgaagta agaagcaact    600

gtcgacaagt cgccttggtt atttcgtgtt gttttaactg aacctcgaca taagcctttt    660

ggatcgaagg ttaaacgatc cgctcctcgc ttgagcttga ggcggcgtat ctcttatgtc    720

aacagagaca ctttggtcta tggttgtata acaatagata gactcccgtt tgcaagatta    780

gggttaacag atcttgccgt tagtctggtt agcgcgtaac cggccttgat ttatggaata    840

gatccattgt ccaatggctt tgccaatgga acgccgacgt ggctgtataa tacgtcgttg    900

acaagtacga aatcttgtta gtgtttttcc ctccacttaa atcgaagggt tttgttttgg    960

tcttcccgaa cgcatacgtt agtgtgacta ccgttgttcg aaacaagtaa aacaggaagg   1020

gggttcgaat ccctccctaa ccgcgggtaa gcggccca                           1058
```

```
<210> SEQ ID NO 5
<211> LENGTH: 6355
<212> TYPE: DNA
<213> ORGANISM: Artificial Sequence
<220> FEATURE:
<223> OTHER INFORMATION: Description of Artificial Sequence: cDNA copy
      of the nucleotide sequence of the genome of TMV-U2

<400> SEQUENCE: 5

gatgttttaa tagttttcga caacaacaat taaaacaaaa acaacatatt acaaacaaca     60

aacaacaaca atggcacaca tacaatctat aattagcaac gcccttcttg aaagcgtgag    120

tggtaaaaac actctcgtta atgaccttgc aagaaggcgc atgtacgata cggccgtgga    180

agaatttaac gcccgcgacc gtagaccaaa ggtcaacttt tccaaaacta ttagcgaaga    240

gcaaacgctt ctagtctcca acgcgtaccc ggagttccag attacctttt ataatactca    300

aaatgccgta cacagtttgg ctggaggttt gagagcatta gaattggaat atctgatgct    360

acaagttccc tatggatcgc cgacatatga tataggtggg aactttgcag cacatttgtt    420

caaaggcagg gattacgtgc attgctgtat gcccaatctg gacatacgag atataatgag    480

gcacgaagga caaaaggact caattgagat gtatttgtcc agattgtctc gttctaacaa    540

ggtaattcct gagtttcaaa gggaggcttt taacaggtat gcagaagctc ccaacgaagt    600

ctgctgctct aaaacttttc aggattgtcg aatacatccg ccagagaata gtggtagaag    660

atacgctgtt gctctgcaca gtttgtatga tattcctgtg catgagtttg gagctgcgtt    720

aatatctaag aatatacatg tatgttatgc agcttccatt ttggcagaag cattattact    780

agaccagacg gaggttacgc ttaatgaaat aggcgcaact ttcaaaagag aaggtgatga    840

tgtttctttt ttctttgctg atgaaagtac tttaaattat agtcataaat acaaaaatat    900

cttgcattat gtagttaaat cttactttcc tgcttctagt agaatagttt actttaagga    960

atttttagtc actagggtta atacttggtt ttgtaaattt accaaagtag atacctatat   1020

tctgtacaag agtgttagac aagtagggtg tgatagtgat cagttctatg aggcgatgga   1080

agacgccttt gcttacaaga aaaccttggc catgttcaac actgaaagag caatctttag   1140

agacacggct tcggttaact tttggttccc taagatgaag gacatggtga tagtaccgct   1200

gtttgagggt tctattacca gcaaaaagat gacaaggagt gaggtcattg ttaatcgtga   1260

cttcgtttac acagtgctta atcatatcag aacatatcaa gccaaagcgt taacttacca   1320

gaacgtatta tctttcgtgg agtctataag atcccgcgtg ataatcaatg gtgttactgc   1380

taggtctgaa tgggatgtag ataaagcaat tcttcaaccc ttgtcaatga ctttcttctt   1440

gcagactaag ctggctgcgc ttcaagacga tatagtaatg ggaaagtttc ggtgcttgga   1500
```

-continued

```
taagaccact tctgaactta tttgggatga ggtgggcaaa ttttttggaa acgttttccc   1560
cactatcaaa gagagattgg tgagcaggaa aattctggat gtaagtgaga atgctctgaa   1620
gatcaagatc ccagatctgt atgtcacatg gaaagacagg ttcgtagctg aatacaccaa   1680
gtctgaggag ttaccgcatc tagatatcaa gaaggactta gaagaagctg agcaaatgta   1740
cgacgcgtta tcagaattat ctatccttaa gggtgctgat aatttcgata tcgcgaagtt   1800
caaagacatg tgcaaggctt tagatgttag tcctgatgtg gcagcacgag taatcgttgc   1860
agtggccgag aatagaagcg gtttaactct tacttttgat aagccaaccg aggagaatgt   1920
ggctaaggct cttaaaagca cggcgtctga ggccgtggta tgtcttgaac cgacatccga   1980
agaggtgaac gtaaataaat tttctattgc tgagaaaggg agattgcctg tgtgtgcaga   2040
aagtcatggt ttgacgaatg ctaacttaga gcaccaggag ttggagtccc tcaacgattt   2100
ccataaggct tgcgtggata gtgtgattac aaagcaaatg gcatcggttg tctacactgg   2160
ctcactcaaa gttcaacaaa tgaagaacta tgtggacagt ttggcagctt cgttgtccgc   2220
cactgtatca aatctatgca agtcactaaa ggatgaagtc gggtatgatt ctgattccag   2280
ggagaaagtt ggtgtttggg atgtcacttt gaaaaagtgg ctcctcaaac ctgcggccaa   2340
aggtcattca tggggagttg tcctggatta caaggggaaa atgtttactg cacttctatc   2400
ttatgaagga gatagaatgg tgactgagag cgactggagg agggtggctg tatcatctga   2460
tacaatggta tattctgata ttgcaaagct ccaaaatctg aggaaaacaa tgagagacgg   2520
tgaaccccac gaacctactg caaagatggt acttgtggat ggggtgcctg gttgtggaaa   2580
gtacaaagga gattttgaaa gatttgatct tgatgaggat ttgatcttgg ttcctggaaa   2640
acaagctgct gctatgatca gaagaagggc taattcatct ggactgataa gagccacaat   2700
ggacaatgtg agaacggtag attcacttct aatgcatcca aaaccgcgat cacacaagag   2760
gctttttatt gatgaagggt tgatgctgca caccggttgt gttaacttcc tggtgcttat   2820
ctctggttgc gacatcgcat acatttacgg agatacacag cagattcctt tcattaacag   2880
agttcagaat ttcccgtatc ccaaacattt tgagaagctg caagtggatg aagttgagat   2940
gaggaggacc acactgagat gcccaggtga tgtgaatttt ttcctacaat cgaagtacga   3000
aggagcggtg acaaccactt caactgtaca acgatcggtc tcatctgaga tgataggcgg   3060
taagggagta ctaaacagtg tttccaaacc actaaaaggg aaaattgtaa ctttcactca   3120
ggctgataaa tttgagttag aggagaaggg ctataagaat gtgaacaccg ttcatgagat   3180
ccaaggagaa acctttgaag atgtgtcgct ggtcagattg acggcaactc cactgactct   3240
gatttccaag tcttccccgc atgttctagt cgctctgact agacacacaa agagcttcaa   3300
atattacacc gtagtgttag atcctttagt acagataatt agtgatttgt cttctttaag   3360
ctccttcctt ttagaaatgt atatggtaga agcaggtagt agatagcaat tacagatgga   3420
tgcagtgttc aaaggtcata atctctttgt ggcaacacct aaatcaggag actttccaga   3480
tctacagttc tattacgatg tatgcctccc tggtaatagt actatactta acaagtatga   3540
tgctgttacc atgaggttac gtgataatag tcttaatgtg aaggattgtg ttcttgattt   3600
ttccaaaagt attccgatgc caaaggaggt gaaaccatgt ctagagccag ttttgcgtac   3660
cgcggcggaa ccgccaaggg ctgcaggact actcgaaaat ctggttgcaa tgattaaaag   3720
aaatttcaac gcaccagacc tgacggggac gattgacatt gagagcaccg catctgttgt   3780
agtagataag ttttttgata gctattttat taaaaaagaa aaatacacaa aaaatattgc   3840
```

-continued

```
tggagtgatg acgaaggatt caatgatgag atggttggaa aacaggaaag aagtactatt   3900
ggacgacttg gctaactaca attttacaga tctgccggcc atcgatcagt acaagcacat   3960
gatcaaggct caaccaaaac agaaattgga cctttcaatt cagaatgaat accctgctct   4020
gcaaacaatt gtctaccatt cgaagcagat caacggtatt ttggccggtt tctcagagct   4080
tacaaggttg ctgctcgagg catttgattc taagaagttt cttttcttta ctaggaaaac   4140
tccagaacag attcaagaat tttctcgga tctcgactcg cacgttccta tggatgtgtt   4200
agaactggat atttctaagt atgataagtc acagaacgag tttcattgtg ctgtagagta   4260
tgaaatatgg aaaagattgg gtctcaatga gtttttggcc gaagtgtgga aacaagggca   4320
caggaaaaca actttgaagg attacattgc tggaatcaag acatgtctgt ggtatcaaag   4380
gaaaagcggt gatgtgacta ctttcatcgg caatactgtt ataatagcag cttgcttggg   4440
ttcaatgtta ccgatggaaa aggtcataaa aggtgctttt tgtggagacg attccgtttt   4500
gtattttcca aagggtttgg atttccctga cattcagtca tgtgctaatc tcatgtggaa   4560
ttttgaggcc aaactgtata gaaagaggta cggttacttt tgtggtagat acatcataca   4620
ccatgataag ggagcaatag tgtattatga tcctttgaag ttgatctcca aacttggggc   4680
aaaacatatc aaggattatg atcacttaga agagttaagg gtgtctttgt gcgatgttgc   4740
ttgttcgctc ggaaactggt gcttaggctt tccgcagctg aacgcagcta tcaaggaggt   4800
tcataaaacc gcgattgatg gttcgtttgc ttttaattgt gttaacaaat ttttgtgtga   4860
taaattttta tttagaactt tgtttttaaa tggctgttag tctcagagat actgtcaaaa   4920
ttagcgagtt cattgatctt tcgaaacagg atgagatact tccggcattc atgactaagg   4980
tcaagagtgt tagaatatcg actgtggaca agattatggc tgttaagaat gatagtcttt   5040
ctgatgtaga tttacttaaa ggtgttaagt tagttaagaa agggtatgtg tgcttagctg   5100
atttggtagt gtctggggag tggaatctcc cggataactg ccgtggtggt gtcagtgttt   5160
gtattgtaga taagagaatg aaaaggagta aggaagcaac gctgggtgcg tatcacgccc   5220
ctgcttgcaa aaagaatttt tcttttaagc taatccctaa ttattcaata acatccgagg   5280
atgctgagaa gcacccgtgg caagtgttag tgaatatcaa aggagtggct atggaagaag   5340
gatactgtcc tttatctttg gagttcgttt caatttgtgt agtacataaa aataatgtaa   5400
gaaaaggttt gagggaacgt attttgagtg tgacagacgg ctcgccaatt gaactcactg   5460
aaaaggttgt tgaggagttc gtggatgaag taccaatggc tgtgaaactc gaaaaggttc   5520
cggaaaacaa aaaagaaatg gtaggtaata atgttaataa taagaaaata aataacagtg   5580
gtaagaaggg ttttaaaatt gaggaaattg aggataatgt aagtgatgac gagtctatcg   5640
cgtcatcgag tacgttttaa tcaatatgcc ttatacaatc aactctccga gccaatttgt   5700
ttacttatct tccgcttacg cagatcctgt gcagctgatc aatctgtgta caaatgcatt   5760
gggtaaccag tttcaaacgc aacaagctag gacaacagtc caacagcaat ttgcggatgc   5820
ctggaaacct gtgcctagta tgacagtgag atttcctgca tcggatttct atgtgtatag   5880
atataattcg acgcttgatc cgttgatcac ggcgttatta aatagctttg atactagaaa   5940
tagaataata gaggttgata atcaacccgc accgaatact actgaaatcg ttaacgcgac   6000
tcagagggta gacgatgcta ctgtagctat aagggcttca atcaataatt tggctaatga   6060
actggttcgt ggaactggca tgttcaatca agcaggcttt gagactgcta gtggacttgt   6120
ctggaccaca actccggcta cttagctatt gttgtgagat ttcctaaaat aaagtcgctg   6180
aagacttaaa attcagggtg gctgatacca aaatcagcag tggttgttcg tccacttaaa   6240
```

-continued tataacgatt gtcatatctg gatccaacag ttaaaccatg tgatggtgta tactgtggta 6300
tggcgtaaaa catcggagag gttcgaatcc tcccctaacc gccggtagcg gccca 6355

<210> SEQ ID NO 6
<211> LENGTH: 2346
<212> TYPE: DNA
<213> ORGANISM: Artificial Sequence
<220> FEATURE:
<223> OTHER INFORMATION: Description of Artificial Sequence: nucleotide sequence of the tomato phytoene desaturase (pds) encoding cDNA

<400> SEQUENCE: 6
cttttactag ttatagcatt cggtatcttt ttctgggtaa ctgccaaacc accacaaatt 60
acaagtttcc atttaactct tcaacttcaa cccaaccaaa tttatttcct taattgtgca 120
gaaccactcc ctatatcttc taggtgcttt cattcgttcc gaggtaagaa aagatttttg 180
tttctttgaa tgctttatgc cactcgttta acttctgagg tttgtggatc ttttaggcga 240
cttttttttt ttttgtatgt aaaatttgtt tcataaatgc ttctcaacat aaatcttgac 300
aaagagaagg aattttacca agtatttagg ttcagaaatg gataattttc ttactgtgaa 360
atatccttat ggcaggtttt actgttattt ttcagtaaaa tgcctcaaat tggacttgtt 420
tctgctgtta acttgagagt ccaaggtagt tcagcttatc tttggagctc gaggtcgtct 480
tctttgggaa ctgaaagtcg agatggttgc ttgcaaagga attcgttatg ttttgctggt 540
agcgaatcaa tgggtcataa gttaaagatt cgtactcccc atgccacgac cagaagattg 600
gttaaggact tggggccttt aaaggtcgta tgcattgatt atccaagacc agagctggac 660
aatacagtta actatttgga ggctgcattt ttatcatcaa cgttccgtgc ttctccgcgc 720
ccaactaaac cattggagat tgttattgct ggtgcaggtt tgggtggttt gtctacagca 780
aaatatttgg cagatgctgg tcacaaaccg atactgctgg aggcaaggga tgttctaggt 840
ggaaaggtag ctgcatggaa agatgatgat ggagattggt acgagactgg tttgcatata 900
ttctttgggg cttacccaaa tattcagaac ctgtttggag aattagggat taacgatcga 960
ttgcaatgga aggaacattc aatgatattt gcaatgccaa gcaagccagg agaattcagc 1020
cgctttgatt tctccgaagc tttacccgct cctttaaatg gaattttagc catcttaaag 1080
aataacgaaa tgcttacatg gccagagaaa gtcaaatttg caattggact cttgccagca 1140
atgcttggag ggcaatctta tgttgaagct caagatggga taagtgttaa ggactggatg 1200
agaaagcaag gtgtgccgga cagggtgaca gatgaggtgt tcattgctat gtcaaaggca 1260
ctcaacttta taaaccctga cgaactttca atgcagtgca ttttgatcgc attgaacagg 1320
tttcttcagg agaaacatgg ttcaaaaatg gccttttttag atggtaatcc tcctgagaga 1380
ctttgcatgc cgattgttga acacattgag tcaaaaggtg gccaagtcag actgaactca 1440
cgaataaaaa agattgagct gaatgaggat ggaagtgtca agagttttat actgagtgac 1500
ggtagtgcaa tcgagggaga tgcttttgtg tttgccgctc cagtggatat tttcaagctt 1560
ctattgcctg aagactggaa agagattcca tatttccaaa agttggagaa gttagtcgga 1620
gtacctgtga taaatgtaca tatatggttt gacagaaaac tgaagaacac atatgatcat 1680
ttgctcttca gcagaagctc actgctcagt gtgtatgctg acatgtctgt tacatgtaag 1740
gaatattaca accccaatca gtctatgttg gaattggttt ttgcacctgc agaagagtgg 1800
atatctcgca gcgactcaga aattattgat gcaacgatga aggaactagc aacgcttttt 1860

-continued

```
cctgatgaaa tttcagcaga tcaaagcaaa gcaaaaatat tgaagtacca tgttgtcaaa   1920

actccgaggt ctgtttataa aactgtgcca ggttgtgaac cctgtcggcc tttacaaaga   1980

tccccaatag aggggtttta tttagccggt gactacacga aacagaaata cttggcttca   2040

atggaaggcg ctgtcttatc aggaaagctt tgtgctcaag ctattgtaca ggattatgag   2100

ttacttgttg gacgtagcca aaagaagttg tcggaagcaa gcgtagttta gctttgtggt   2160

tattatttag cttctgtaca ctaaatttat gatgcaagaa gcgttgtaca caacatatag   2220

aagaagagtg cgaggtgaag caagtaggag aaatgttagg aaagctccta tacaaaagga   2280

tggcatgttg aagattagca tctttttaat cccaagttta aatataaagc atattttatg   2340

gaattc                                                              2346
```

<210> SEQ ID NO 7
<211> LENGTH: 7096
<212> TYPE: DNA
<213> ORGANISM: Artificial Sequence
<220> FEATURE:
<223> OTHER INFORMATION: Description of Artificial Sequence: nucleotide sequence of the tobacco nitrate reductase (nia-2) encoding cDNA

<400> SEQUENCE: 7

```
tacatacaag ggcgcgaata aacttttttt aaagtaaatg tatatgaact tgcaatgaaa     60

gaggacctta acttgtttgt ctttgttgct ttctgcaaat ttcaccttaa cagcccattt    120

gagattgatt tagttagtta taacaattag ttaaatgctt gtgtaatttg aagaaaatat    180

ttggacgtgc tcgctgaaaa cattatactc ctatataata gaaatacttt ctgaaaagtt    240

ggtcttgttc aaaaacgtat aagagagttg gtcttctcat aaatagtcac tagctttctg    300

atttttttc actttctata tcacgtaaat aggtactcaa atttgatatt tacaccaaac    360

aaatgaaaat aggatatgtg tttttcatac gtatatttat ctatcgtact taatgataca    420

tacatataca tataacctta ctttttgatt actaaaaatt taattatatt taatttgggt    480

aaatatcaga tgccacaaaa catttaccta gccactgttt ttgactacta aaaatttaat    540

tatgtttagc ttgggtaaat atcagatgtc actaaacatt ttacctagcc attcctccga    600

aaagaaattg agaaggaaat tagagttagt ggagccataa taatgtttaa tgtgaccata    660

actcggtgaa aaccacggca agaataagaa acagctgtta aggctaacca acagctgcat    720

atctttaagc catttgctat taccccaaca tcgcatcttc ctctgatccc gaccctacgg    780

gcgtaaaaag tgtaaatcgt tagaattgtt ttatttattt tatgatgtca ctattttta    840

aaatcaaaat taaattgggg tgtcgatttt tttgggtcct gcttatgtat agtatggcgc    900

tatggaggca ctgagagagt ccgaaacgtt tctatataag gccaccccac gcattcacaa    960

acttcgttcc caaacagaac aagaaaatca aatctcggag agagagagag agaaatattt   1020

tgagagagaa atacagaaaa tctctcttcc ttctttcctt ttttttcaa tccccattca   1080

tattcttttt ttagaataat ctatggcggc atctgtcgaa aacaggcagt tcagtcacct   1140

agaagccggt ttatcccggt ctttcaagcc ccggtctgat tccccggttc gtggctgcaa   1200

cttcccttcg cccaacagta ctaatttcca aaagaaacca aattccacca tttaccttga   1260

ttactcgtcg agtgaagacg acgatgatga tgacgaaaaa aatgagtacc ttcaaatgat   1320

taaaaaaggg aattcagagt tagagccatc tgttcatgac actagggacg aaggtaccgc   1380

tgataattgg attgaacgca acttttccat gattcgtctc accggaaagc atccatttaa   1440

ctccgaacca ccgttgaacc ggctcatgca ccacggcttt atcacaccgg tcccacttca   1500
```

-continued

```
ttacgttcgt aaccatggac cggttcccaa gggcacgtgg gatgactgga ccgtggaagt   1560
cacgggacta gtgaagcgtc ctatgaaatt cacaatggac cagttggtta acgaattccc   1620
ttgtagagaa ttgcccgtta cgcttgtttg tgctggcaat cgaaggaaag aacagaacat   1680
ggttaaacaa accattggtt tcaactgggg cgccgctgcc gtttcaacaa cgatatggcg   1740
cggggtaccc ctccgcgctt tgctaaaacg gtgcggtgtt tttagcaaga ataaaggggc   1800
gcttaatgtt tgcttcgaag gagctgatgt gttgcccgga ggtggtggtt caaagtatgg   1860
aaccagcatt aagaaggaat ttgcaatgga tccagcacga gatatcatcg tagcctacat   1920
gcagaacgga gaaaaattgg cacccgacca cgggtttcca gtacgaatga taattccagg   1980
attcattgga ggaagaatgg tgaaatggat aaagaggatt atagtcacca cccaagaatc   2040
agacagctat tatcatttca aggacaatag agttcttcct ccccatgttg atgctgaact   2100
tgcaaatacc gaaggtacgt accgtaacta tttcaattta ttactccatt tgttccaatt   2160
tatgtgaacc tatttccttt ttggtccgtt caaaaaagaa tgaacccttt ctaaatttgg   2220
taacaattta gcttaaactt acaacttcac ccttaatgag aaacttttat aaccacacaa   2280
ataccctggg gcccatttgg acttgtttag gtcgacaaat tccaaaagtt ttattttttt   2340
cttaaacttc gtgctcagtc aaacaggttc acgtaaattg aaacggagag agtatcattt   2400
ttattaaggg gtataaatat attttaatta gttgagactt gcacatacaa gtaaaatatt   2460
tcttagaata caaaatcaac tgaaagctta cttctaatta tatggttttg aattttcctt   2520
tcaatgaagt aaataaaaag gaaacaatta tattcaacgc atgtaggtat atggtcctgt   2580
cattatctca aatcaaatgg tttaaagaca aaggactttg gaaacataga attgtcagct   2640
ttatagttat ggagtactat attagttagc tgtttgcatc tattcataat tggtctatct   2700
gtgtgcagca tggtggtaca agccagagta tatcatcaat gagcttaata ttaactctgt   2760
cattacgacg ccgtgtcatg aagaaatttt gccaattaac gcctggacga ctcagcgacc   2820
ttacacgttg aggggctatt cttattctgg ttagtatttt tatattttcc gattttgctg   2880
agaatatcat atttcttagt tttgtcgata catcgtatcc tctaactctg acgttttact   2940
tcgtccttat gcacccactt acgtccttac tttctcagac agtttattga tgaaaactac   3000
ttactatttt cgacccgata gcctcagcgt ccttaattaa atgtgatgtt ttgaaagaga   3060
tattctctcc cgtctatttt aattaatttt tggctgtttt tatacgtggg aatctatttt   3120
taacattaat taatatagaa atgaaccata ttaatattat taatttcttc attgaaaata   3180
caacaaatac tcttcggctc ttactacaat gacaattttg aagaaaaata attaattcct   3240
tcctaatatc tgaaaaatca aatattgtgg accataaaaa aaggtcaaaa aattaattaa   3300
aatgaactgg agagagtaaa ttagaaaata taattatagc actagtaatt aaagttatta   3360
gatgtcttct ttaaaaagcg tgtgaaaact ttaaagacga aatataatat gaatattatc   3420
taatacttag aaagtgtcaa taattggtag acaatttaaa ctatatacta gttaaaaagt   3480
ctgtcaatac aactattagt attggggatt agagagaata gtagtaaaat ggagtaattg   3540
gacgcatgag cttgggcatg ctgattgctg tcagcttgtt tgctaatgtg aaaaagaaaa   3600
tagtaagaaa aggccaacat ggttttgttt attttattat gtggtagtac acaaaaacct   3660
ggggagcttt cctagttctg aagagtcggt ctttggtagc acaaaattaa tagtatagta   3720
taccaagtga atattaaatt caattgtcta aagcacggaa tctttttgac tactttagtt   3780
cctgcatctt gggttgcctc aacaacaccc tttattgaat tattatagta atgttcaata   3840
```

-continued

```
taatatacaa ttagaaaaca ctctaagtgg tcactttata tggatctagt caatactatt   3900
tcttctaaac aacgtgccta attacttccc actttccagt acatgaccac cattaagttt   3960
aatttttgtc aattccttgt gcaattggcc cttcaaatga gcagaagtgt tacgtaggaa   4020
aactaacttc agctactatt ataggagtaa acctgttagg aaaagatgct cgaggaactg   4080
acaaaacttg tagaataatt agccattgta ttgattgaaa tactgattgt gaacgtgtaa   4140
caaacaggcg gagggaaaaa agtaacgcga gtagaagtga cgttggatgg aggagaaaca   4200
tggcaagtta gcacactaga tcacccagag aagcccacca aatatggcaa gtactggtgt   4260
tggtgctttt ggtcactcga ggttgaggtg ttagacttgc tcagtgctaa agaaattgct   4320
gttcgagctt gggatgagac cctcaatact caacccgaga agcttatttg gaacgtcatg   4380
gtacgttcac ttcttctttt acctttattt cttttaactt ctatatacta gcggtgtaaa   4440
gttattttac accataagtt aacttacaaa aatatgtaac tatttatact acgagtgatg   4500
agggcaagaa ggggtttaag tatttgacaa taaatgtaaa ccctgcaatt ttgttcctaa   4560
tttttatcc tttcaactct ttgtgattgc ttcattatct agattcacag agcacatgtg   4620
ttcacatgcc aaaacaaaaa actacaaaca aaaaaacttt tcactagctt tagtctaaga   4680
ttccccttt tttttttggg aggtgtgtgg tccatactcc atagatcaat tccagccact   4740
gacgtaccaa accctgaaaa ttcctagtag ttatagcgac gtacaatcat ttcatattat   4800
gtaagcagag acgtgatcac atgaactaga tgtgaatacc acttgcccag tccaccaggt   4860
caattcatct agatgtgtaa atcttgacac cagcactggg tcacttttat aacactagca   4920
tttaacaaca tttcatcctt gaacattact tgggctaatt aataagtatt tttttttata   4980
tactctaaaa attgtaatta cataaatgaa tttaacttat acacgctgac aatgttacta   5040
attccacttt ttacggacgg ttatctatag aaatcattta ggtgaaacaa ttctcttaca   5100
ctatgatcag tgttagtaca taatggttat tacattttct aaatattgtg ctatgttgca   5160
atgttcaggg aatgatgaat aattgctggt tccgagtaaa gatgaatgtg tgcaagcctc   5220
acaagggaga gattggaata gtgtttgagc atccgactca acctggaaac caatcaggtg   5280
gatggatggc gaaggagaga catttggaga tatcagcaga ggcacctcaa acactaaaga   5340
agagtatctc aactccattc atgaacacag cttccaagat gtactccatg tccgaggtca   5400
ggaaacacag ctctgctgac tctgcttgga tcatagtcca tggtcatatc tatgacgcca   5460
cgcgtttctt gaaagatcac cctggtggga ctgacagcat tctcatcaat gctggcactg   5520
attgcactga ggaatttgat gcaattcatt ctgataaggc taagaagctc ttggaggatt   5580
tcaggattgg tgaactcata actactggtt acacctctga ctctcctggc aactccgtgc   5640
acggatcttc ttccttcagc agctttctag cacctattaa ggaacttgtt ccagcgcaga   5700
ggagtgtggc cctaattcca agagagaaaa tcccatgcaa actcatcgac aagcaatcca   5760
tctcccatga tgttaggaaa tttcgatttg cattgccctc tgaggatcaa gtcttgggct   5820
tgcctgttgg aaaacatatc ttcctctgtg ccgttattga cgataagctc tgcatgcgcg   5880
cttacacgcc tactagcacg atcgatgagg tggggtactt cgagttggtt gtcaagatat   5940
acttcaaagg aattcaccct aaattcccca atggagggca aatgtcacag tatcttgatt   6000
ctatgccgtt agggtcattt ctcgacgtga aaggtccatt aggtcacatt gaataccaag   6060
gaaagggaaa tttcttagtt catggcaaac agaagtttgc caagaagttg gccatgatag   6120
caggtggaac aggaataact ccagtgtatc aagtcatgca ggcaattctg aaagatccag   6180
aagatgacac agaaatgtat gtggtgtatg ctaacagaac agaggatgat attttactta   6240
```

-continued

```
aggaagagct tgattcatgg gctgagaaaa ttccagagag ggttaaagtt tggtatgtgg   6300

ttcaggattc tattaaagaa ggatggaagt acagcattgg ttttattaca gaagccattt   6360

tgagagaaca tatccctgag ccatctcaca caacactggc tttggcttgt ggaccacctc   6420

ctatgattca atttgctgtt aatccaaact tggagaagat gggctatgac attaaggatt   6480

ccttattggt gttctaattt taaaaacaaa acaatatctg caggaataaa ttttttttt    6540

ccccctatca gttgtacata ttgtatttgg tttatcaccc ccatgtacta cgtagtgttt   6600

gtagttctta catttttatt ttttagaatt tttttaaacc ttaggatata aaggttttct   6660

cttccaacaa agtgattctt tagggaagaa atgtactgta ctgtactagt atgtctaagc   6720

cgaaagttgt aatgtttacc atgacaaatt gtattcaatt cctcatggaa tagtaacatt   6780

gtgttcatgt gtcttcctgt aagcgatctt caaaatatca atgtatatat atagtaattg   6840

caaaccattg ttccttttcc cgatgtagtt aactactctt tctttagctt ctagtctctg   6900

gtgaatattt ttttttctat aactctttaa ttaatacggc cttaaataag agaaaagttt   6960

aaaccacgaa tatcattatg cagacgtata ggtaattaat ctactttttg aaaaaaaatc   7020

tattttcttt atgtggtcct tcaaaataat attctagaac cttttgtata ttccctttta   7080

acttctattt agtttt                                                    7096
```

<210> SEQ ID NO 8
<211> LENGTH: 1839
<212> TYPE: DNA
<213> ORGANISM: Artificial Sequence
<220> FEATURE:
<223> OTHER INFORMATION: Description of Artificial Sequence: nucleotide sequence of the tobacco nitrite reductase (nir-1) encoding cDNA

<400> SEQUENCE: 8

```
tttctattaa atttctggca ccttcattgc caaatccagc tagattttcc aagaatgctg     60

tcaagctcca cgcaactccg ccgtctgtgg cagcgccgcc agctggtgct ccagaggttg    120

ctgctgagag gctagaaccc agagttgagg aaaaagatgg ttattggata ctcaaggagc    180

agtttagaaa aggcataaat cctcaagaaa aggtcaagat tgagaagcaa cctatgaagt    240

tgttcatgga aaatggtatt gaagagcttg ctaagatacc cattgaagag atagatcagt    300

ccaagcttac taaggatgat attgatgtta ggcttaagtg gcttggcctc ttccatagga    360

gaaagaacca atatgggcgg ttcatgatga gattgaagct tccaaatgga gtaacaacga    420

gtgcacagac tcgatacttg gcgagtgtga taaggaaata cgggaaagaa ggatgtgctg    480

atattacaac gaggcaaaat tggcagattc gtggagttgt actgcctgat gtgcccgaga    540

tactaaaggg actagcagaa gttgggttga ccagtttgca gagtggcatg gacaatgtca    600

ggaatccagt aggaaatcct cttgctggaa ttgatccaga agaaatagta gacacagggc    660

cttacactaa tttgctctcc caatttatca ctggcaattc acgaggcaat cccgcagttt    720

ctaacttgcc aaggaagtgg aatccgtgcg tagtaggctc tcatgatctt tatgaacatc    780

cccatatcaa cgatctcgcg tacatgcctg ccacgaaaga tggacgattt ggattcaacc    840

tgcttgtggg tgggttcttc agcgcaaaaa gatgtgatga ggcaattcct cttgatgcat    900

gggttccagc tgatgatgtt gttccggttt gcaaagcaat actggaagct tttagagatc    960

ttggtttcag agggaacaga cagaaatgta gaatgatgtg gttaatcgat gaactgggtg   1020

tagaaggatt cagggcagag gtcgagaaga gaatgccaca gcaagagcta gagagagcat   1080
```

-continued

```
ctccagagga cttggttcag aaacaatggg aaagaagaga ttatcttggt gtacatccac   1140

aaaaacaaga aggctacagc tttattggtc ttcacattcc agtgggtcgt gttcaagcag   1200

acgatatgga tgagctagct cgtttagctg atgagtatgg ttcaggagag atccggctta   1260

ctgtggaaca aaacattatt attcccaaca ttgagaactc aaagattgag gcactgctca   1320

aagagcctgt tctgagcaca ttttcacctg atccacctat tctcatgaaa ggtttagtgg   1380

cttgtactgg taaccagttt tgtggacaag ccataatcga gactaaagct cgttccctga   1440

tgataactga agaggttcaa cggcaagttt ctttgacacg gccagtgagg atgcactgga   1500

caggctgccc gaatacgtgt gcacaagttc aagttgcgga cattggattc atgggatgcc   1560

tgactagaga taagaatgga aagactgtgg aaggcgccga tgttttctta ggaggcagaa   1620

tagggagtga ttcacatttg ggagaagtat ataagaaggc tgttccttgt gatgatttgg   1680

taccacttgt tgtggactta ctagttaaca actttggtgc agttccacga gaaagagaag   1740

aaacagaaga ctaataaaat ttagaatagt tggtgatttt gctgtgttca taacatgtaa   1800

tgtatgataa atcaatgcaa acatttctac ctacgtgag                          1839
```

<210> SEQ ID NO 9
<211> LENGTH: 1294
<212> TYPE: DNA
<213> ORGANISM: Artificial Sequence
<220> FEATURE:
<223> OTHER INFORMATION: Description of Artificial Sequence: cDNA of the beta-1,3-glucanase of Nicotiana plumbagenifolia

<400> SEQUENCE: 9

```
ttgctcttca aatggctgct attatactgc taggattgct tgtttccagc actgagatag     60

taggagctca atcagtaggt gtttgctacg gaatgctggg caacaacttg ccaccagcat    120

cacaagttgt acaactgtac aagtcaaaaa acataagaag aatgaggctt tatgatccaa    180

atcaagcagc tttacaggct ttaagaggct ccaacattga agttatgtta ggagttccca    240

attcagatct ccaaaacatt gctgctaacc cctcaaatgc aaataattgg gtccagagga    300

atgtcagaaa tttctggcca gccgttaaat ttaggtacat tgccgttgga aatgaagtca    360

gccctgtaac aggcacatct tcacttaccc gatatcttct tccggccatg aggaacattc    420

ggaatgcgat ttcttcagca ggtttgcaaa acaatatcaa agtctcaagt tctgtagaca    480

tgaccttgat tgggaactct tttccaccat cacagggttc gtttaggaac gacgttaggt    540

cgttcattga tccgattatt gggtttgtaa ggcgcataaa ttcgccttta ctcgttaaca    600

tttatcctta ttttagctat gctggtaatc cgcgcgatat ttctctcccc tatgctcttt    660

tcactgctcc aaatgtggtg gtacaagatg gttcacttgg atatagaaac ttatttgatg    720

caatgtcgga tgctgtgtat gctgccctgt ctcgagccgg agggggctcg atagagattg    780

ttgtgtccga gagtggctgg ccatctgctg gcgcatttgc cgcgacaaca aacaatgcag    840

caacttacta caagaactta attcagcatg ttaaaagggg tagtccaaga aggcctaata    900

aagtcattga gacctattta tttgctatgt ttgatgagaa taacaaaaac cctgaattgg    960

agaaacattt tggactcttt tcccccaaca agcagcccaa atatccactc agctttgggt   1020

tttcagatag atattgggac atttctgctg aaaataatgc tactgcagct tctctcataa   1080

gtgagatgtg ataagagagt tctctttaaa tatctttaca tggatggaaa acttagtacc   1140

aataactaga ttgtttcttt ctttatgcaa ttttcttgta atgagagact agtacttgct   1200

ctctgtgtcc ttgtggagag taactagaga caaattaagc aaataacata aataattgag   1260
```

-continued tgttgattct gcaatgataa atagaaaaaa aaaa 1294

<210> SEQ ID NO 10
<211> LENGTH: 720
<212> TYPE: DNA
<213> ORGANISM: Artificial Sequence
<220> FEATURE:
<223> OTHER INFORMATION: Description of Artificial Sequence: green fluorescent protein encoding regon

<400> SEQUENCE: 10
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 11
<211> LENGTH: 1809
<212> TYPE: DNA
<213> ORGANISM: Artificial Sequence
<220> FEATURE:
<223> OTHER INFORMATION: Description of Artificial Sequence:beta-glucuronidase encoding region

<400> SEQUENCE: 11
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtatc accgtttgtg tgaacaacga actgaactgg 420
cagactatcc cgccgggaat ggtgattacc gacgaaaacg gcaagaaaaa gcagtcttac 480
ttccatgatt tctttaacta tgccggaatc catcgcagcg taatgctcta caccacgccg 540
aacacctggg tggacgatat caccgtggtg acgcatgtcg cgcaagactg taaccacgcg 600
tctgttgact ggcaggtggt ggccaatggt gatgtcagcg ttgaactgcg tgatgcggat 660
caacaggtgg ttgcaactgg acaaggcact agcgggactt tgcaagtggt gaatccgcac 720
ctctggcaac cgggtgaagg ttatctctat gaactgtgcg tcacagccaa aagccagaca 780
gagtgtgata tctacccgct tcgcgtcggc atccggtcag tggcagtgaa gggcgaacag 840
ttcctgatta accacaaacc gttctacttt actggctttg gtcgtcatga agatgcggac 900
ttacgtggca aaggattcga taacgtgctg atggtgcacg accacgcatt aatggactgg 960

-continued attggggcca actcctaccg tacctcgcat taccottacg ctgaagagat gctcgactgg 1020
gcagatgaac atggcatcgt ggtgattgat gaaactgctg ctgtcggctt taacctctct 1080
ttaggcattg gtttcgaagc gggcaacaag ccgaaagaac tgtacagcga agaggcagtc 1140
aacggggaaa ctcagcaagc gcacttacag gcgattaaag agctgatagc gcgtgacaaa 1200
aaccacccaa gcgtggtgat gtggagtatt gccaacgaac cggatacccg tccgcaagtg 1260
cacgggaata tttcgccact ggcggaagca acgcgtaaac tcgacccgac gcgtccgatc 1320
acctgcgtca atgtaatgtt ctgcgacgct cacaccgata ccatcagcga tctctttgat 1380
gtgctgtgcc tgaaccgtta ttacggatgg tatgtccaaa gcggcgattt ggaaacggca 1440
gagaaggtac tggaaaaaga acttctggcc tggcaggaga aactgcatca gccgattatc 1500
atcaccgaat acggcgtgga tacgttagcc gggctgcact caatgtacac cgacatgtgg 1560
agtgaagagt atcagtgtgc atggctggat atgtatcacc gcgtctttga tcgcgtcagc 1620
gccgtcgtcg gtgaacaggt atggaatttc gccgattttg cgacctcgca aggcatattg 1680
cgcgttggcg gtaacaagaa agggatcttc actcgcgacc gcaaaccgaa gtcggcggct 1740
tttctgctgc aaaaacgctg gactggcatg aacttcggtg aaaaaccgca gcagggaggc 1800
aaacaatga 1809

<210> SEQ ID NO 12
<211> LENGTH: 411
<212> TYPE: DNA
<213> ORGANISM: Artificial Sequence
<220> FEATURE:
<223> OTHER INFORMATION: Description of Artificial Sequence: cDNA copy of part of the region of a TMV-U2 variant comprising the origin of assembly

<400> SEQUENCE: 12
ccctcgccaa ttgaactcac tgaaaaagtt gttgatgagt tcgtagatga agtaccgatg 60
gctgtgaaac tcgaaaggtt ccggaaaaca aaaaagagag tggtaggtaa taatgttaat 120
aataagaaaa taaataatag tggtaagaag ggtttgaaag ttgaggaaat tgaggataat 180
gtaagtgatg acgagtctat cgcgtcatcg agtacgtttt aatcaatatg ccttatacaa 240
tcaactctcc gagccaattt gtttacttaa gttccgctta tgcagatcct gtgcagctga 300
tcaatctgtg tacaaatgca ttaggtaacc agtttcaaac gcaacaagct aggacaacag 360
tccaacagca atttgcggat gcctggaaac ctgtgcctag tatgacagtg a 411

<210> SEQ ID NO 13
<211> LENGTH: 198
<212> TYPE: DNA
<213> ORGANISM: Artificial Sequence
<220> FEATURE:
<223> OTHER INFORMATION: Description of Artificial Sequence: cDNA copy of STMV leader region

<400> SEQUENCE: 13
agtaaaactt accaatcaaa agacctaacc aacaggactg tcgtggtcat ttatgctgtt 60
gggggacata gggggaaaac atattgcctt cttctacaag aggccttcag tcgccataat 120
tacttggcgc ccaattttgg gtttcagttg ctgtttccag ctatggggag aggtaaggtt 180
aaaccaaacc gtaaatcg 198

<210> SEQ ID NO 14
<211> LENGTH: 455

-continued

<212> TYPE: DNA
<213> ORGANISM: Artificial Sequence
<220> FEATURE:
<223> OTHER INFORMATION: Description of Artificial Sequence:cDNA copy of STMV trailer region

<400> SEQUENCE: 14

```
gacaagtcgc cttggttatt tcgtgttgtt ttaactgaac ctcgacataa gccttttgga     60
tcgaaggtta aacgatccgc tcctcgcttg agcttgaggc ggcgtatctc ttatgtcaac    120
agagacactt tggtctatgg ttgtataaca atagatagac tcccgtttgc aagattaggg    180
ttaacagatc ttgccgttag tctggttagc gcgtaaccgg ccttgattta tggaatagat    240
ccattgtcca atggctttgc caatggaacg ccgacgtggc tgtataatac gtcgttgaca    300
agtacgaaat cttgttagtg tttttccctc cacttaaatc gaagggtttt gttttggtct    360
tcccgaacgc atacgttagt gtgactaccg ttgttcgaaa caagtaaaac aggaaggggg    420
ttcgaatccc tccctaaccg cgggtaagcg gccca                               455
```

<210> SEQ ID NO 15
<211> LENGTH: 1971
<212> TYPE: DNA
<213> ORGANISM: Artificial Sequence
<220> FEATURE:
<223> OTHER INFORMATION: Description of Artificial Sequence: cDNA copy of part of the genome of a TMV-U1 variant, comprising MP and CP genes

<400> SEQUENCE: 15

```
ggaaacactg tgattatagc tgcatgtttg gcctcgatgc ttccgatgga gaaaataatc     60
aaaggagcct tttgtggtga cgatagtctg ctgtacttcc caaagggttg tgagtttccg    120
gatgtgcaac actccgcgaa tcttatgtgg aattttgaag caaaactgtt taaaaaacag    180
tatggatact tttgcggaag gtatgtaata catcacgaca gaggatgcat tgtgtattac    240
gatcccctaa agttgatctc gaaacttggt gctaaacaca tcaaggattg ggaacacttg    300
gaggagttca gaaggtctct ttgtgatgtt gctgtttcgt tgaacaattg tgcgtattac    360
acacagttgg acgacgctgt atgggaggtt cataagaccg cccctccagg ttcgtttgtt    420
tataaaagtc tggtgaagta tttgtctgat aaagttcttt ttagaagttt gtttatagat    480
ggctctagtt gttaaaggaa aagtgaatat caatgagttt atcgacctga caaaaatgga    540
gaagatctta ccgtcgatgt ttacccctgt aaagagtgtc atgtgttcca aagttgataa    600
aataatggtt catgagaatg agtcattgtc agaggtaaac cttctcaaag gagttaagct    660
tattgatagt ggatacgtct gtttagccgg tttggtcgtc acgggcgagt ggaacttgcc    720
tgacaattgc agaggaggtg tgagcgtgtg tctggtggac aaaaggatgg aaagagccga    780
cgaggccact ctcggatctt actacacagc agctgcaaag aaaagatttc agttcaaggt    840
cgttcccaat tatgctataa ccacccagga cgcgatgaaa aacgtctggc aagttttagt    900
caatattaga aatgtaaaga tgtcagcggg tttctgtccg ctttctctgg agtttgtgtc    960
ggtgtgtatc gtttatagaa ataatataaa attaggtttg agagagaaga tcacaagtgt   1020
gagagatgga gggcccatgg aacttacaga agaagttgtt gatgagttca tggaagatgt   1080
ccctatgtca atcaggcttg caaagtttcg atctcgaacc ggaaaaaaga gtgatgtccg   1140
taaagggaaa attagtagta gtgatcggtc agcgccgaac aagaactata gaaatgttaa   1200
ggattttgga ggaatgagtt ttaaaaagaa taatttaatc gatgatgatt cggagactac   1260
tgtcgccgaa tcggattcgt tttaaatatg tcttacagta tcactactcc atctcagttc   1320
```

-continued

```
gtgttcttgt cagcagcgtg ggccgaccca atagagttaa ttaatttatg tactaatgcc   1380
ttaggaaatc agtttcaaac acaacaagct cgaactgtcg ttcaaagaca attcagtgag   1440
gtgtggaaac cttcaccaca agtgactgtt aggttccctg acagtgactt taaggtgtac   1500
aggtacaatg cggtattaga cccgctagtc acagcactgt taggtgcatt tgacactaga   1560
aatagaataa tagaagttga aaatcaggcg aaccccacaa ctgccgaaac gttagatgct   1620
actcgtagag tagacgacgc aacggtggcc ataaggagcg ctataaataa tttagtagta   1680
gaattgatca gaggaaccgg atcttataat cggagctctt tcgagagctc ttctggtttg   1740
gtttggaact ctggtcctgc aacttgaggt agtcaagatg cataataaat aacggattgt   1800
gtccgtaatc acacgtggtg cgtacgataa cgcatagtgt ttttccctcc acttaaatcg   1860
aagggttgtg tcttggatcg cgcgggtcaa atgtatatgg ttcatataca tccgcaggca   1920
cgtaataaag cgaggggttc gaatcccccc gttacccccg gtaggggccc a             1971
```

What is claimed is:

1. A method for the introduction of inhibitory RNA in the cytoplasm of a plant cell, said inhibitory RNA reducing or abolishing the expression of a gene in the plant cell, said method comprising:

a) introducing into said plant cell, a viral RNA vector derived from satellite tobacco mosaic virus, wherein said vector comprises said inhibitory RNA and an origin of assembly of tobacco mosaic virus wherein said inhibitory RNA comprises a sense RNA or an antisense RNA, said sense or antisense RNA comprising a nucleotide sequence of at least 50 nucleotides having 95% to 100% sequence identity to the nucleotide sequence of a target gene in said plant cell; and b) introducing a corresponding helper virus into said plant cell.

2. The method of claim 1, wherein said helper virus is tobacco mosaic virus.

3. A method for the introduction of inhibitory RNA into the cytoplasm of a plant cell, said inhibitory RNA reducing or abolishing the expression of a gene in the plant cell, said method comprising:

a) introducing into said plant cell a viral RNA vector derived from satellite tobacco necrosis virus, wherein said vector comprises said inhibitory RNA and an origin of assembly of tobacco mosaic virus wherein said inhibitory RNA comprises a sense RNA or an antisense RNA, said sense or antisense RNA comprising a nucleotide sequence of at least 50 nucleotides having 95% to 100% sequence identity to the nucleotide sequence of a target gene in said plant cell; and b) introducing a corresponding helper virus into said plant cell, wherein said helper virus is derived from tobacco necrosis virus and comprises a coat protein gene of tobacco mosaic virus.

4. The method of claim 3, wherein said satellite RNA virus is satellite tobacco necrosis vector strain 1 or 2 and said helper virus is derived from TNV-A.

5. The method of claim 3, wherein said satellite RNA virus is STNV-C and said helper virus is derived from TNV-D.

6. A kit for the introduction of inhibitory RNA in the cytoplasm of a plant cell, said inhibitory RNA reducing or abolishing the expression of a gene in the plant cell, said kit comprising a) a viral RNA vector derived from satellite tobacco mosaic virus, wherein said vector comprises said inhibitory RNA and an origin of assembly of tobacco mosaic virus wherein said inhibitory RNA comprises a sense RNA or an antisense RNA, said sense or antisense RNA comprising a nucleotide sequence of at least 50 nucleotides having 95% to 100% sequence identity to the nucleotide sequence of a target gene in said plant cell; and b) a corresponding helper virus.

7. The kit of claim 6, wherein said corresponding helper virus is tobacco mosaic virus.

8. A kit for the introduction of inhibitory RNA into the cytoplasm of a plant cell, said inhibitory RNA reducing or abolishing the expression of a gene in the plant cell, said kit comprising:

a) a viral RNA vector derived from satellite tobacco necrosis virus, wherein said vector comprises said inhibitory RNA and an origin of assembly of tobacco mosaic virus wherein said inhibitory RNA comprises a sense RNA or an antisense RNA, said sense or antisense RNA comprising a nucleotide sequence of at least 50 nucleotides having 95% to 100% sequence identity to the nucleotide sequence of a target gene in said plant cell; and b) a corresponding helper virus derived from tobacco necrosis virus, said virus comprising the coat protein gene of tobacco mosaic virus.

9. The kit of claim 8, wherein said satellite RNA virus is satellite tobacco necrosis vector strain 1 or 2 and said corresponding helper virus is derived from TNV-A.

10. The kit of claim 8, wherein said satellite RNA virus is STNV-C and said corresponding helper virus is derived from TNV-D.

11. The method of claim 1, wherein said origin of assembly from tobacco mosaic virus has the nucleotide sequence of SEQ ID No 2 from the nucleotide at position 5443 to the nucleotide at position 5518.

12. The method of claim 1, wherein said origin of assembly from tobacco mosaic virus has the nucleotide sequence of SEQ ID No 5 from the nucleotide at position 5430 to the nucleotide at position 5505.

13. The method of claim 1, wherein said origin of assembly from tobacco mosaic virus has the nucleotide sequence of SEQ ID No 12.

14. The method of claim 1, wherein said viral RNA vector further comprises a STMV leader having the nucleotide sequence of SEQ ID No 4 from the nucleotide at position 1 to the nucleotide at position 197.

15. The kit of claim 6, wherein said origin of assembly from tobacco mosaic virus has the nucleotide sequence of SEQ ID No 2 from the nucleotide at position 5443 to the nucleotide at position 5518.

16. The kit of claim 6, wherein said origin of assembly from tobacco mosaic virus has the nucleotide sequence of SEQ ID No 5 from the nucleotide at position 5430 to the nucleotide at position 5505.

17. The kit of claim 6, wherein said origin of assembly from tobacco mosaic virus has the nucleotide sequence of SEQ ID No 12.

18. The kit of claim 6, wherein said viral RNA vector further comprises a STMV leader having the nucleotide sequence of SEQ ID No 4 from the nucleotide at position 1 to the nucleotide at position 197.

19. The method of claim 1 or 3, wherein said sense RNA or said antisense RNA comprises a nucleotide sequence of at least 100 nucleotides having at least 95% to 100% sequence identity of the nucleotide sequence of a target gene in said plant cell.

20. The kit of claim 6 or 8, wherein said sense RNA or said antisense RNA comprises a nucleotide sequence of at least 100 nucleotides having at least 95% to 100% sequence identity of the nucleotide sequence of a target gene in said plant cell.

21. The method of claim 1, wherein said sense RNA or said antisense RNA comprises a nucleotide sequence of at least 100 nucleotides having at least 95% to 100% sequence identity of the nucleotide sequence of a target gene in said plant cell, and wherein said helper virus is tobacco mosaic virus.

22. The method of claim 3, wherein said sense RNA or said antisense RNA comprises a nucleotide sequence of at least 100 nucleotides having at least 95% to 100% sequence identity of the nucleotide sequence of a target gene in said plant cell, and wherein said satellite RNA virus is satellite tobacco necrosis vector strain 1 or 2 and said helper virus is derived from TNV-A.

23. The method of claim 3, wherein said sense RNA or said antisense RNA comprises a nucleotide sequence of at least 100 nucleotides having at least 95% to 100% sequence identity of the nucleotide sequence of a target gene in said plant cell, wherein said satellite RNA virus is STNV-C and said helper virus is derived from TNV-D.

24. The method of claim 19 wherein said plant is selected from *Nicotinia* spp, *Oryza sativa, Zea Mays, Brassica* spp., *Gossypium* spp., *Triticum* spp., *Arabidopsis* spp. or *Petunia* spp.

25. The kit of claim 6, wherein said sense RNA or said antisense RNA comprises a nucleotide sequence of at least 100 nucleotides having at least 95% to 100% sequence identity of the nucleotide sequence of a target gene in said plant cell, and wherein said corresponding helper virus is tobacco mosaic virus.

26. The kit of claim 8, wherein said sense RNA or said antisense RNA comprises a nucleotide sequence of at least 100 nucleotides having at least 95% to 100% sequence identity of the nucleotide sequence of a target gene in said plant cell, and wherein said satellite RNA virus is satellite tobacco necrosis vector strain 1 or 2 and said corresponding helper virus is derived from TNV-A.

27. The kit of claim 8, wherein said sense RNA or said antisense RNA comprises a nucleotide sequence of at least 100 nucleotides having at least 95% to 100% sequence identity of the nucleotide sequence of a target gene in said plant cell, and wherein said satellite RNA virus is STNV-C and said corresponding helper virus is derived from TNV-D.

28. The kit of claim 20, wherein said origin of assembly from tobacco mosaic virus has the nucleotide sequence of SEQ ID No 2 from the nucleotide at position 5443 to the nucleotide at position 5518.

29. The kit of claim 20, wherein said origin of assembly from tobacco mosaic virus has the nucleotide sequence of SEQ ID No 5 from the nucleotide at position 5430 to the nucleotide at position 5505.

30. The kit of claim 20, wherein said origin of assembly from tobacco mosaic virus has the nucleotide sequence of SEQ ID No 12.

31. The kit of claim 6, wherein said sense RNA or said antisense RNA comprises a nucleotide sequence of at least 100 nucleotides having at least 95% to 100% sequence identity of the nucleotide sequence of a target gene in said plant cell, and wherein said viral RNA vector further comprises a STMV leader having the nucleotide sequence of SEQ ID No 4 from the nucleotide at position 1 to the nucleotide at position 197.

32. The method of any one of claims 1, 2, 3 to 5, and 12, wherein said plant is selected from *Nicotinia* spp, *Oryza sativa, Zea Mays, Brassica* spp., *Gossypium* spp., *Triticum* spp., *Arabidopsis* spp. or *Petunia* spp.

* * * * *